(12) United States Patent
Parker et al.

(10) Patent No.: US 12,377,164 B2
(45) Date of Patent: Aug. 5, 2025

(54) LINKERS AND CONJUGATES

(71) Applicants: ASTRAZENECA AB, Sodertalje (SE); CAMBRIDGE ENTERPRISE LIMITED, Cambridgeshire (GB)

(72) Inventors: Jeremy Stephen Parker, Macclesfield (GB); Hannah Fiona Sore, Cambridgeshire (GB); David Robert Spring, Cambridgeshire (GB); Stephen James Walsh, Cambridgeshire (GB)

(73) Assignees: ASTRAZENECA AB, Sodertalje (SE); CAMBRIDGE ENTERPRISE LIMITED, Cambridge (GB)

( * ) Notice: Subject to any disclaimer, the term of this patent is extended or adjusted under 35 U.S.C. 154(b) by 1118 days.

(21) Appl. No.: 17/264,721

(22) PCT Filed: Jul. 31, 2018

(86) PCT No.: PCT/EP2018/070703
§ 371 (c)(1),
(2) Date: Jan. 29, 2021

(87) PCT Pub. No.: WO2020/025108
PCT Pub. Date: Feb. 6, 2020

(65) Prior Publication Data
US 2021/0308275 A1 Oct. 7, 2021

(51) Int. Cl.
| | | |
|---|---|---|
| A61K 47/68 | (2017.01) | |
| A61K 31/704 | (2006.01) | |
| A61K 38/07 | (2006.01) | |
| A61K 47/54 | (2017.01) | |
| A61P 35/00 | (2006.01) | |
| C07D 239/42 | (2006.01) | |

(52) U.S. Cl.
CPC ........ *A61K 47/6889* (2017.08); *A61K 31/704* (2013.01); *A61K 38/07* (2013.01); *A61K 47/545* (2017.08); *A61K 47/68031* (2023.08); *A61K 47/6851* (2017.08); *A61P 35/00* (2018.01); *C07D 239/42* (2013.01)

(58) Field of Classification Search
CPC .. A61K 47/6851; A61K 31/704; A61K 38/07; A61K 47/545; A61K 47/6803; A61K 47/6889; A61K 47/6809; A61K 47/6811; A61K 47/6855; A61K 47/60; A61K 47/65; A61P 35/00; C07D 239/42
See application file for complete search history.

(56) References Cited
U.S. PATENT DOCUMENTS

| | | | |
|---|---|---|---|
| 4,816,567 A | 3/1989 | Cabilly et al. | |
| 5,079,361 A * | 1/1992 | Alexander | C07D 213/30 544/242 |
| 5,439,950 A | 8/1995 | Liao et al. | |
| 2012/0005204 A1 | 1/2012 | Diaz et al. | |

FOREIGN PATENT DOCUMENTS

| | | | |
|---|---|---|---|
| WO | WO 1988/005433 A1 | 7/1988 | |
| WO | WO 2007/085930 A1 | 8/2007 | |
| WO | WO 2010/070300 A2 | 6/2010 | |
| WO | WO 2016/067021 A1 | 5/2016 | |
| WO | WO 2017/186894 A1 | 11/2017 | |
| WO | WO-2018218004 A1 * | 11/2018 | ............. A61K 31/40 |

OTHER PUBLICATIONS

Behrens, et al., Mol. Pharm. 2015 12(11):3986 (Year: 2015).*
Burke, et al., Bioconjugate Chem. 2009 20:1242 (Year: 2009).*
MedChem 2017; product page for N3-PEG3-VC-PAB-MMAE; URL https://www.medchemexpress.com/N3-PEG3-vc-PAB-MMAE.html accessed Apr. 29, 2024 (Year: 2017).*
Broadpharm 2017; Product page for Propargyl-PEG4-Bromide; URL https://broadpharm.com/product/bp-22782 accessed Apr. 29, 2024 (Year: 2017).*
Wang, et al., Peptide-drug conjugates as effective prodrug strategies for targeted delivery, Advanced Drug Delivery Reviews 110-111 (2017) 112-126.
Nunes, et al., Functional native disulfide bridging enables delivery of a potent, stable and targeted antibody-drug conjugate (ADC), Chem. Commun., 2015, 51, 10624-10627.
Maruani, et al., A plug-and-play approach to antibody-based therapeutics via a chemoselective dual click strategy, Nature Communications, 2015, pp. 1-9.
Lyon, et al., Self-hydrolyzing maleimides improve the stability and pharmacological properties of antibody-drug conjugates, Nature biotechnology vol. 32 No. 10 Oct. 2014, pp. 1059-1065.
Chudasama, et al., Bromopyridazinedione-mediated protein and peptide bioconjugation, Chem. Commun., 2011, 47, 8781-8783.

(Continued)

*Primary Examiner* — Julie Wu
*Assistant Examiner* — Sydney Van Druff
(74) *Attorney, Agent, or Firm* — Stites & Harbison PLLC; Richard S. Myers, Jr.

(57) ABSTRACT

A conjugate comprising a protein or a peptide, a linker and an active agent, wherein the linker comprises the moiety of formula (III): (III) wherein two of $A^1$, $A^2$ and $A^3$ are N and the other of $A^1$, $A^2$ and $A^3$ is CH; X is selected from N, O and S, and Pep indicates where the moiety is linked to the protein or peptide, either directly or indirectly.

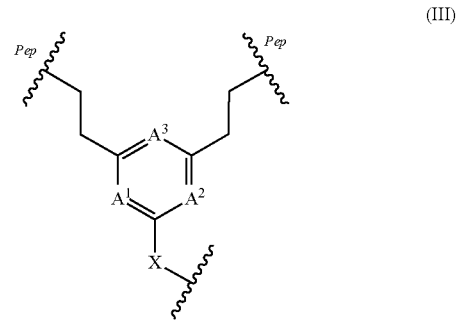

(III)

20 Claims, 2 Drawing Sheets

(56) References Cited

OTHER PUBLICATIONS

Chudasama, et al., Recent advances in the construction of antibody-drug conjugates, Nature Chemistry | vol. 8 Feb. 2016, pp. 114-119.
Winther, et al., Quantification of Thiols and Disulfides, Biochim Biophys Acta. Feb. 2014 ; 1840(2), pp. 1-26.
Zimmerman, et al., Production of Site-Specific Antibody-Drug Conjugates Using Optimized Non-Natural Amino Acids in a Cell-Free Expression System, Bioconjugate Chem. 2014, 25, 351-361.
Junutula, et al., Site-specific conjugation of a cytotoxic drug to an antibody improves the therapeutic index, Nature Biotechnology vol. 26 No. 8 Aug. 2008, pp. 925-932.
Beck, et al., Strategies and challenges for the next generation of antibody-drug conjugates, Nature Reviews | Drug Discovery vol. 16 | May 2017 | pp. 315-337.
Schumacher, et al., Next generation maleimides enable the controlled assembly of antibody-drug conjugates via native disulfide bond bridging, Org. Biomol. Chem., 2014, 12, 7261-7269.
Kohler, et al., Continuous cultures of fused cells secreting antibody of predefined specificity; Nature 256 (5517): 495-497 (1975).
Dubowchik, et al., Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity, Bioconjugate Chem, 2002, 13, 855-869.
Marks, et al., By-passing Immunization Human Antibodies from V-gene Libraries Displayed on Phage, J. Afoz. Riol. (1991) 222, 581-597.
Lonberg, N., Fully human antibodies from transgenic mouse and phage display platforms, Current Opinion in Immunology 2008, 20:450-459.
Miller, et al., Design, Construction, and In Vitro Analyses of Multivalent Antibodies, J Immunol 2003; 170:4854-4861.
Clackson, et al., Making antibody fragments using phage display libraries, Nature, vol. 352, 1991, pp. 625-628.
Li,e t al., Divinylsuifonamides as Specific Linkers for Stapling Disulfide Bonds in Peptides, Org Letters, 2017, 19, 4972-4975.
Badescu, et al., Bridging Disulfides for Stable and Defined Antibody Drug Conjugates, Bioconjugate Chem. 2014, 25, 1124-1136.
Behrens, et al., Antibody-Drug Conjugates (ADCs) Derived from Interchain Cysteine Cross-Linking Demonstrate Improved Homogeneity and Other Pharmacological Properties over Conventional Heterogeneous ADCs, Mol. Pharmaceutics 2015, 12, 3986-3998.
Chen, et al., Design and synthesis of novel iminothiazinylbutadienols and divinylpyrimidinethiones as ARE inducers, Bioorg Med Chem Lett. Feb. 1, 2014; 24(3): 940-943.
Sebastiano, et al., A new deuterated alkylating agent for quantitative proteomics, Rapid Commun. Mass Spectrom. 2003; 17: 2380-2386.
Walsh, et al., BIOL 304: Site-selective generation of stable antibody-drug conjugates via cysteine bridging of native antibodies, 256th ACS National Meeting & Exposition, 2018; pp. 1-2.

\* cited by examiner

LINKERS AND CONJUGATES

CROSS REFERENCE TO RELATED APPLICATIONS

This application is a § 371 National State Application of PCT/EP2020/070703 filed Jul. 31, 2018.

The present invention relates to protein and peptide conjugates, and methods of manufacturing the same. More especially, the present invention relates to providing a protein or peptide, linker and an active agent, for example a drug or labelling moiety, to produce a conjugate. Additionally, the present invention provides an improved linker for use in conjugates and methods of introducing said linker into said conjugates. More specifically, the conjugate may be an antibody conjugate, such as an antibody drug conjugate (ADC).

Protein drug conjugates, in particular antibody drug conjugates, are known to provide targeted delivery of highly potent drugs to specific tissue for treatment. More specifically, ADCs, which typically consist of an antibody linked via a chemical linker to a biologically active cytotoxic or drug payload, are known for use in anticancer treatments. The targeted delivery offered by such protein drug conjugates results from the ability of the antibody or the like to sensitively discriminate between healthy and diseased tissue, thus ensuring safe delivery of the highly potent drug.

There are currently four ADCs on the market and over 60 others in clinical trials (Beck 2017). However, current approaches for ADC production still have numerous shortcomings and greatly influence an ADCs stability, drug-antibody ratio (DAR) and drug distribution. Nucleophilic bioconjugation at cysteine or lysine residues is pseudorandom, leading to the formation of ADCs that are heterogeneous in terms of the number of cytotoxin molecules incorporated (the DAR) and their locations on the antibody. In addition, the linkage formed via commonly utilized maleimide conjugation to cysteine residues is unstable in circulation leading to premature dissociation of the antibody payload. Such heterogeneous and/or unstable ADCs are associated with unreliable pharmacokinetic profiles and toxic side effects.

The plasma stability of maleimide-based linkers has been increased by hydrolysis of the succinimide thioether ring through linker modifications or antibody engineering (Lyon 2014). However, an inherently stable linker is preferential. The development of new ADC formats to enable site-selective antibody modification, including the incorporation of engineered cysteine residues (Junutula 2008) and unnatural amino acids (Zimmerman 2014) into the antibody sequence and the use of various enzymatic processes (Chudasama 2016) have produced ADCs with precise DAR and defined attachment points. While effective, these methods are complicated and generally inefficient (Schumacher 2014).

Recently, disulfide-bridging linkers have emerged for ADC production: a bis-reactive linker moiety undergoes reaction with both thiol residues derived from a reduced cysteine disulfide bond, leading to covalent re-bridging of the protein (Badescu 2014). Such linkers are capable of generating ADCs with more precise DAR and drug distribution as well as reforming covalent bonds between the antibody chains (Schumacher 2014, Behrens 2015, Maruani 2015).

Of these, dibromomaleimide (DBM) linkers are the most significant; however, cysteine re-bridging reactions with DBM linkers are reversible, thus premature payload release remains a potential issue (Nunes 2015, Chudasma 2011).

While ADCs are well-known in the art, other protein drug conjugates comprising a protein with the ability to provide targeted delivery of a drug payload are not as well-known. For example, albumin may offer a suitable alternative to antibodies in such protein drug conjugates.

Albumin consists of three structurally homologous, largely helical domains (I, II and III), each consisting of two subdomains, A and B. Like other mammalian albumins, human albumin contains 17 disulfide bridges and a free thiol at Cys34, which provides the largest fraction of free thiol in blood serum.

Additionally, peptide drug conjugates (PDCs) are known and are described, for example, in Wang 2017.

As well as drug conjugates, the linking of labelling moieties such as fluorophores and biotin tags to proteins and peptides can be useful in techniques such as flow cytometry, Immunofluorescence staining and immunohistochemical staining.

The present invention aims to provide a disulfide bridging linker platform which addresses the reported stability issues yet retains the advantages of a precise ratio between the active agent and the protein or peptide, and ability to distribute the active agent.

Accordingly, in a first aspect of the present invention, there is provided a conjugate comprising a protein or a peptide, a linker and an active agent, wherein the linker comprises the moiety of formula (III):

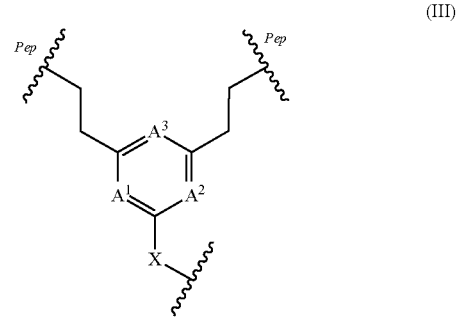

(III)

wherein two of $A^1$, $A^2$ and $A^3$ are N and the other of $A^1$, $A^2$ and $A^3$ is CH;

X is selected from N, O and S, and

Pep indicates where the moiety is linked to the protein or peptide, either directly or indirectly.

The present invention provides a linker for use in conjugates, with utility in linking proteins or peptides and active agents, for example antibodies and cytotoxins to provide ADC molecules. The linker provides an improved targeted payload of the active agent, and thus may improve the activity of the conjugate where the active agent exerts a biological activity, such as cytotoxicity. Additionally or alternatively, the linker provides the conjugate with increased stability as compared to currently known linker molecules for use in conjugates. This may improve the tolerability of such conjugates.

The linker may be directly bound to the thio group of a cysteine residue in the peptide or protein, such as an antibody. The linker may re-bridge reduced disulfide bonds in the protein or may be used to staple a peptide.

In a second aspect of the present invention, there is provided an agent-linker compound comprising a linker and an active agent, wherein the linker comprises the moiety of formula (II):

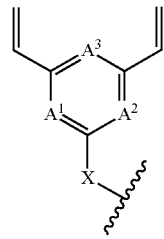

(II)

wherein two of $A^1$, $A^2$ and $A^3$ are N and the other of $A^1$, $A^2$ and $A^3$ is CH;

X is selected from N, O and S.

This agent-linker may be reacted with a protein or a peptide to form the conjugate of the first aspect of the invention.

In a third aspect of the present invention, there is provided a compound of formula (Ia):

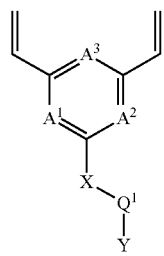

(Ia)

wherein two of $A^1$, $A^2$ and $A^3$ are N and the other of $A^1$, $A^2$ and $A^3$ is CH;

X is selected from $NR^N$, O and S, where $R^N$ is H or $C_{1-2}$ alkyl;

$Q^1$ is:

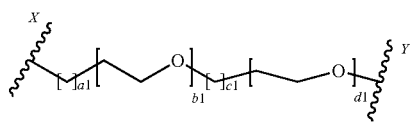

where a1=0 to 5, b1=0 to 16, c1=0 to 5, d1 is 0 to 16, and b1+d1=0 to 16; and

Y is a group capable reacting with another moiety to form a functional linking moiety.

The compound of the third aspect is a precursor of the agent-linker compound of the second aspect of the invention. The agent-linker compound can be formed by reacting the compound with an active agent, which may have a linker group already attached.

In a fourth aspect of the present invention, there is provided a compound of formula (Ib):

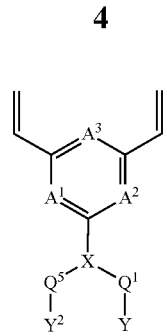

(Ib)

wherein two of $A^1$, $A^2$ and $A^3$ are N and the other of $A^1$, $A^2$ and $A^3$ is CH;

X is N;

$Q^1$ is:

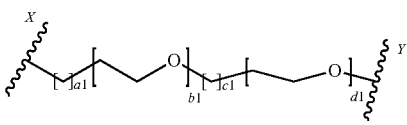

where a1=0 to 5, b1=0 to 16, c1=0 to 5, d1 is 0 to 16, and b1+d1=0 to 16; and

Y is a group capable reacting with another moiety to form a functional linking moiety;

$Q^5$ is:

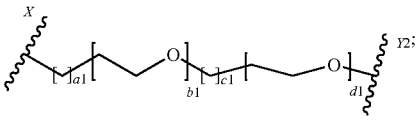

and $Y^2$ a group capable reacting with another moiety to form a functional linking moiety.

The compound of the fourth aspect is a precursor of the agent-linker compound of the second aspect of the invention. The agent-linker compound can be formed by reacting the compound with two active agents, which may have a linker group already attached.

In a fifth aspect of the present invention, there is provided a compound of formula (Ic):

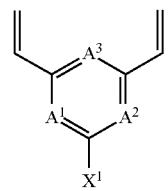

(Ic)

wherein two of $A^1$, $A^2$ and $A^3$ are N and the other of $A^1$, $A^2$ and $A^3$ is CH;

$X^1$ is selected from $NH_2$, OH and SH. This compound is a precursor of the compounds of the third and fourth aspects, which may be formed by reaction with additional linking moieties.

In a sixth aspect of the present invention, there is provided a pharmaceutical composition comprising, a conjugate of the first aspect of the invention, where the active agent is a drug, and a carrier, excipient or diluent. The sixth aspect also provides a conjugate of the first aspect of the invention, where the active agent is a drug, for use in a method of treatment.

In a seventh aspect of the present invention there is provided the use of a conjugate of the first aspect of the invention, where the active agent is a cytotoxic drug, in the manufacture of a medicament for treating a proliferative disease. The seventh aspect also provides a conjugate of the first aspect of the invention, where the active agent is a cytotoxic drug, for use in the treatment of a proliferative disease. The seventh aspect also provides a method of treating a proliferative disease comprising administering a therapeutically effective amount of a conjugate of the first aspect of the invention, where the active agent is a cytotoxic drug, to a patient in need thereof.

Definitions

In the context of the present invention, the term "protein" should be construed to cover any protein which has targeting capabilities and so has the ability to deliver a payload to a specific target tissue. Accordingly, "proteins" include antibodies and fragments thereof, albumin and transferrin, as well as any other alternatives known for use in conjugates. Proteins suitable for use in the present invention may be globular proteins.

The protein or peptide may specifically binds to a target molecule. In some embodiments, they may be a fragment of an antibody that contains at least one target molecule-binding site, lymphokines, hormones, growth factors, or any other cell binding molecule or substance that can specifically bind to a target.

The terms "specifically binds" and "specific binding" refer to the binding of an antibody or other protein, polypeptide or peptide to a predetermined molecule (e.g., an antigen). Typically, the antibody or other molecule binds with an affinity of at least about $1 \times 10^7$ M$^{-1}$, and binds to the predetermined molecule with an affinity that is at least two-fold greater than its affinity for binding to a non-specific molecule (e.g., BSA, casein) other than the predetermined molecule or a closely-related molecule.

Peptides

In one embodiment, the peptide is a linear or cyclic peptide comprising 2-50, preferably 4-30, and more preferably 6-20, contiguous amino acid residues.

Antibodies

The term "antibody" herein is used in the broadest sense and specifically covers monoclonal antibodies, polyclonal antibodies, dimers, multimers, multispecific antibodies (e.g., bispecific antibodies), multivalent antibodies and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include chimeric antibodies, humanized antibodies and human antibodies.

Examples of cell binding agents include those agents described for use in WO 2007/085930, which is incorporated herein.

Tumour-associate antigens and cognate antibodies for use in embodiments of the present invention are listed below, and are described in more detail on pages 14 to 86 of WO 2017/186894, which is incorporated herein.

Albumin

According to an alternative embodiment of the present invention, the antibody may be substituted for albumin.

Active Agent

The active agent may be a drug or a labelling moiety. The active agent needs to comprise a functional group that can be linked to the linker. Such a group may include an amino group, an imine group or a hydroxy group.

Drug

The drug may be a cytotoxic payload or a therapeutic peptide or polypeptide. In particular, where the protein is an antibody or a fragment thereof and the protein drug conjugate is an ADC, the drug is preferably a cytotoxin. Alternatively, where the protein is albumin, the drug may be a cytotoxin or a therapeutic peptide or polypeptide.

Preferably the cytotoxin is a biologically active cytotoxic material. The cytotoxin may be selected from the group comprising auristatins, maytansinoids, tubulysins, calicheamicins, duocarmycins, pyrrolobenzodiazepines (in particular pyrrolobenzodiazepine dimers), camptothecin analogues and doxorubicin.

However, additionally or alternatively, the cytotoxin could also be selected from other known cytotoxins including ricin subunits and other peptide based cytotoxic materials, although such materials are less commonly utilised in the field of the art.

Labelling Moiety

The labelling moiety may be a fluorophore. Suitable fluorophores include fluorescein isothiocyanate (FITC), phycoerythrin (PE), allophycocyanin (APC), Indocicarbocyanine (Cy5), Indocarbocyanine (Cy3), as well as those known by the trade names Alexa Fluor (such as 350, 405, 488, 532, 546, 568, 594, 647, 680, 700, 750) and DyLight (such as 405, 488, 550, 650, 680, 755, 800).

The labelling moiety may also be a biotin tag, derived from biotin.

Preferences $A^1$, $A^2$ and $A^3$

Two of $A^1$, $A^2$ and $A^3$ are N and the other of $A^1$, $A^2$ and $A^3$ is CH.

In some embodiments, $A^1$ and $A^2$ are N.

In other embodiments, $A^1$ and $A^3$ are N.

X

In some embodiments, X is selected from $NR^N$, O and S, where $R^N$ is H or $C_{1-2}$ alkyl. In these embodiments, only a single active agent can be attached is to X via a linker.

In some of these embodiments, X is $NR^N$. X may be NH, NMe or NEt.

In others of these embodiments, X is O.

In others of these embodiments, X is S.

In some embodiments, X is N. In these embodiments, two active agent can be attached to X via linkers.

Single Link to X

In some embodiments, the link between X and the active agent may comprise the group -$Q^1$-$Y^L$-, where $Q^1$ is connected to X. In these embodiments, the linker comprises the moiety of formula (IIIa):

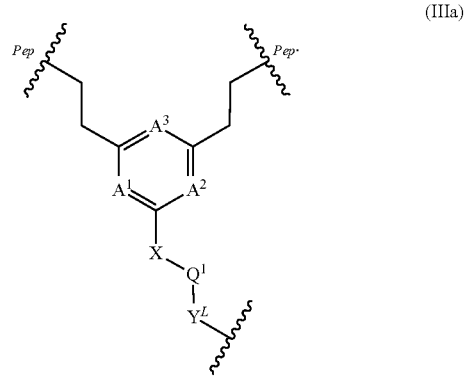

In these embodiments, the agent-linker comprises the moiety of formula (IIa):

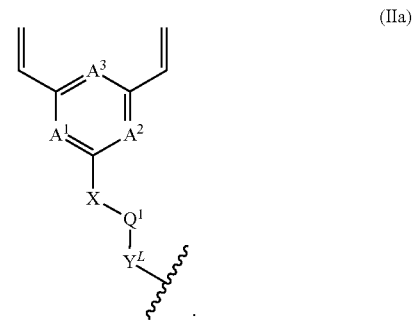

$Q^1$ is:

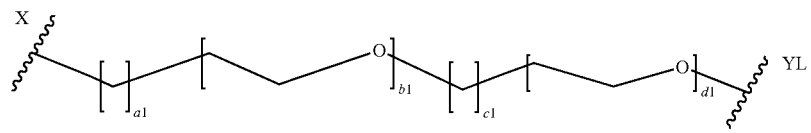

where a1=0 to 5, b1=0 to 16, c1=0 to 5, d1 is 0 to 16, and b1+d1=0 to 16.

$Y^L$ is a functional linking moiety.

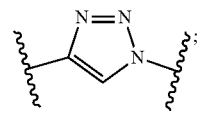 [SMILES: *c1cn(*)nn1]

In some embodiments, $Y^L$ is selected from; and —C(=O)NH—. These groups may be bound in either direction.

In some of these embodiments, $Y^L$ is

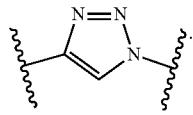 [SMILES: *c1cn(*)nn1]

In other of these embodiments $Y^L$ is —C(=O)NH—.

a1 is 0 to 5. In some embodiments, a1 is 0. In other embodiments, a1 is 1, 2, 3, 4 or 5.

b1 is 0 to 16. In some embodiments, b1 is 0. In other embodiments, b1 is 1, 2, 3, 4, 5, 6, 7, 8, 9, 10, 11, 12, 13, 14 or 15. In some embodiments, b1 is 0 to 8 or 0 to 4.

c1 is 0 to 5. In some embodiments, c1 is 0. In other embodiments, c1 is 1, 2, 3, 4 or 5.

d1 is 0 to 18. In some embodiments, d1 is 0. In other embodiments, d1 is 1, 2, 3, 4, 5, 6, 7, 8, 9, 10, 11, 12, 13, 14 or 15. In some embodiments, d1 is 0 to 8 or 0 to 4.

b1+d1=0 to 16. In some embodiments, b1+d1=0 to 8 or 0 to 4.

In some embodiments, a1 is 3, and b1, c1 and d1 are 0.

In some embodiments, the link between X and the active agent may comprise the group -$Q^1$-$Y^L$-$Q^2$-, where $Q^1$ is connected to X. In these embodiments, the linker comprises the moiety of formula (IIIb):

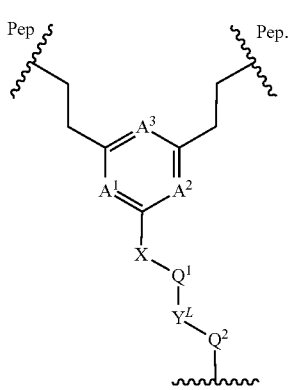

In these embodiments, the agent-linker comprises the moiety of formula (IIb):

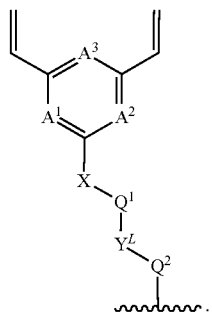

$Q^2$ is:

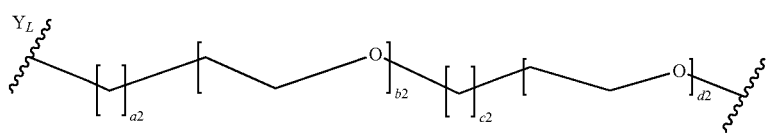

where a2=0 to 5, b2=0 to 16, c2=0 to 5, d2 is 0 to 16, and b2+d2=0 to 16.

a2 is 0 to 5. In some embodiments, a2 is 0. In other embodiments, a2 is 1, 2, 3, 4 or 5.

b2 is 0 to 16. In some embodiments, b2 is 0. In other embodiments, b2 is 1, 2, 3, 4, 5, 6, 7, 8, 9, 10, 11, 12, 13, 14 or 15. In some embodiments, b2 is 0 to 8 or 0 to 4.

c2 is 0 to 5. In some embodiments, c2 is 0. In other embodiments, c2 is 1, 2, 3, 4 or 5.

d2 is 0 to 18. In some embodiments, d2 is 0. In other embodiments, d2 is 1, 2, 3, 4, 5, 6, 7, 8, 9, 10, 11, 12, 13, 14 or 15. In some embodiments, d2 is 0 to 8 or 0 to 4.

b2+d2=0 to 16. In some embodiments, b2+d2=0 to 8 or 0 to 4.

In some embodiments, a2 is 0, b2 is 4, c2 is 1 and d2 is 0.

In other embodiments, b2 is 6, and a2, c2 and d2 are 0.

In other embodiments, all of a2, b2, c2 and d2 are 0, i.e. $Q^2$ is a single bond.

In some embodiments, the link between X and the active agent may comprise the group -$Q^1$-$Y^L$-$Q^2$-$Q^3$-, where $Q^1$ is connected to X and $Q^3$ is linked to the active agent. In these embodiments, the linker comprises the moiety of formula (IIIc):

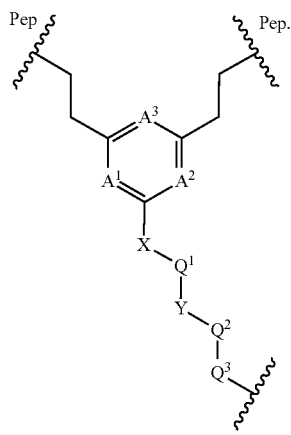

(IIIc)

In these embodiments, the agent-linker is of formula (IIId):

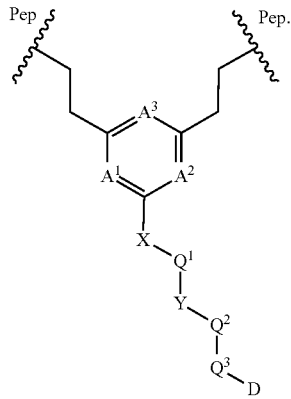

(IIId)

where D is the active agent.

In these embodiments, the agent-linker comprises the moiety of formula (IIc):

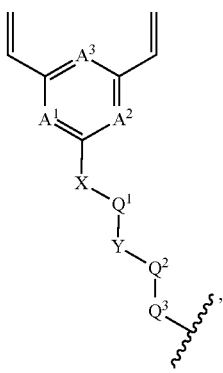

(IIc)

or is of formula (IId):

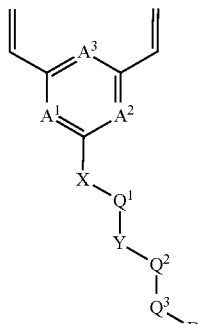

(IId)

$Q^3$ is:

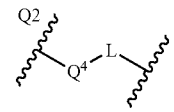

wherein $Q^4$ is a single bond, or

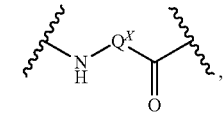

where $Q^X$ is such that $Q^4$ is an amino-acid residue, a dipeptide residue or a tripeptide residue, and L is a group for attachment to the active agent.

In some embodiments, $Q^4$ is a single bond. In some of these embodiments, $Q^2$ may preferably not be a single bond.

In other embodiments, $Q^4$ is

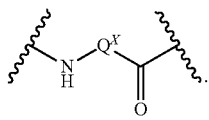

In some of these embodiments, $Q^2$ may be a single bond. $Q^X$

In one embodiment, $Q^4$ is an amino acid residue. The amino acid may a natural amino acids or a non-natural amino acid.

In one embodiment, $Q^4$ is selected from: Phe, Lys, Val, Ala, Cit, Leu, Ile, Arg, and Trp, where Cit is citrulline.

In one embodiment, $Q^4$ comprises a dipeptide residue. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, $Q^4$ is selected from:
$^{NH}$-Phe-Lys-$^{C=O}$,
$^{NH}$Val-Ala-$^{C=O}$,
$^{NH}$Val-Lys-$^{C=O}$
$^{NH}$Ala-Lys-$^{C=O}$,
$^{NH}$-Val-Cit-$^{C=O}$, $^{NH}$-Phe-Cit-$^{C=O}$,
$^{NH}$-Leu-Cit-$^{C=O}$,
$^{NH}$-Ile-Cit-$^{C=O}$,
$^{NH}$-Phe-Arg-$^{C=O}$, and
$^{NH}$-Trp-Cit-$^{C=O}$.
where Cit is citrulline.
Preferably, $Q^4$ is selected from:
$^{NH}$-Phe-Lys-$^{C=O}$,
$^{NH}$-Val-Ala-$^{C=O}$,
$^{NH}$-Val-Lys-$^{C=O}$,
$^{NH}$-Ala-Lys-$^{C=O}$, and
$^{NH}$-Val-Cit-$^{C=O}$.
Most preferably, $Q^4$ is selected from $^{NH}$-Phe-Lys-$^{C=O}$, $^{NH}$-Val-Cit-$^{C=O}$ or $^{NH}$-Val-Ala-$^{C=O}$.
Other dipeptide combinations of interest include:
$^{NH}$-Gly-Gly-$^{C=O}$,
$^{NH}$-Pro-Pro-$^{C=O}$, and
$^{NH}$-Val-Glu-$^{C=O}$.

Other dipeptide combinations may be used, including those described by Dubowchik et al., *Bioconjugate Chemistry*, 2002, 13,855-869, which is incorporated herein by reference.

In some embodiments, $Q^4$ is a tripeptide residue. The amino acids in the tripeptide may be any combination of natural amino acids and non-natural amino acids. In some embodiments, the tripeptide comprises natural amino acids. Where the linker is a cathepsin labile linker, the tripeptide is the site of action for cathepsin-mediated cleavage. The tripeptide then is a recognition site for cathepsin.

In one embodiment, the amino acid side chain is chemically protected, where appropriate. The side chain protecting group may be a group as discussed above. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

In some embodiments, L is selected from:
(a) a single bond;
(b) —C(=O)—;
(c) —NH—; and
(d)

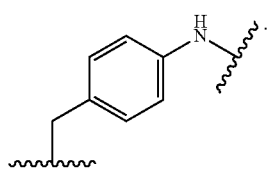 [SMILES: *Cc1ccc(N*)cc1]

In some of these embodiments, L is a single bond. If $Q^4$ is also a single bond, then $Q^3$ is attached directly to the active agent.

In other of these embodiments, L is —C(=O)— or —NH—.

In other of these embodiments, L is

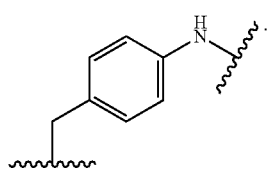 [SMILES: *Cc1ccc(N*)cc1]

This group can act as a self-immolative group in conjunction with a cleavable linking group.

Second Link to X

Where X is N, and there are two active agents linked to X, the second link between X and and active agent may comprise the group $-Q^5-Y^{L2}-$, where $Q^5$ is connected to X. In these embodiments, the linker comprises the moiety of formula (IIIe):

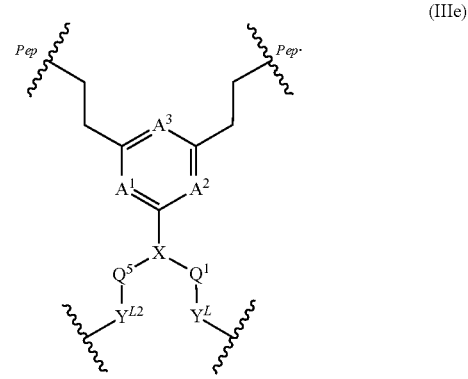

(IIIe)

In these embodiments, the agent-linker comprises the moiety of formula (IIe):

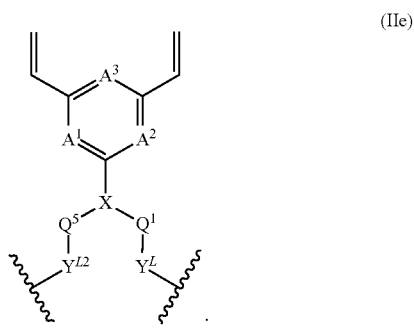

(IIe)

$Q^1$ and $Y^L$ are as described above, and
$Q^5$ is:

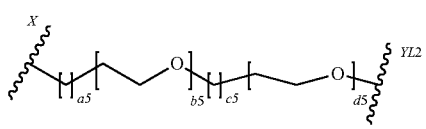

where a5=0 to 5, b5=0 to 16, c5=0 to 5, d5 is 0 to 16, and b5+d5=0 to 16.

$Y^{L2}$ is a functional linking moiety.

In some embodiments, $Y^{L2}$ is selected from

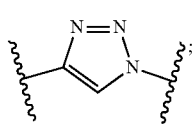 [SMILES: *c1cn(*)nn1]

and —C(=O)NH—. These groups may be bound in either direction.

In some of these embodiments, $Y^{L2}$ is

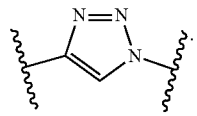 [SMILES: *c1cn(*)nn1]

In other of these embodiments $Y^{L2}$ is —C(═O)NH—.

a5 is 0 to 5. In some embodiments, a5 is 0. In other embodiments, a5 is 1, 2, 3, 4 or 5.

b5 is 0 to 16. In some embodiments, b5 is 0. In other embodiments, b5 is 1, 2, 3, 4, 5, 6, 7, 8, 9, 10, 11, 12, 13, 14 or 15. In some embodiments, b5 is 0 to 8 or 0 to 4.

c5 is 0 to 5. In some embodiments, c5 is 0. In other embodiments, c5 is 1, 2, 3, 4 or 5.

d5 is 0 to 18. In some embodiments, d5 is 0. In other embodiments, d5 is 1, 2, 3, 4, 5, 6, 7, 8, 9, 10, 11, 12, 13, 14 or 15. In some embodiments, d5 is 0 to 8 or 0 to 4.

b5+d5=0 to 16. In some embodiments, b5+d5=0 to 8 or 0 to 4.

In some embodiments, a5 is 3, b5, c5 and d5 are 0.

In some embodiments, the second link between X and an active agent may comprise the group -$Q^5$-$Y^{L2}$-$Q^6$-, where $Q^5$ is connected to X. In these embodiments, the linker comprises the moiety of formula (IIIf):

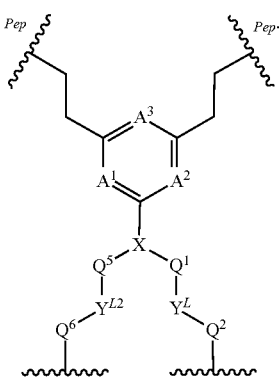

(IIIf)

In these embodiments, the agent-linker comprises the moiety of formula (IIf):

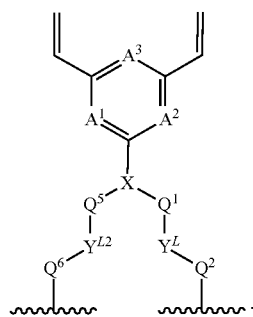

(IIf)

$Q^1$, $Y^L$, $Q^2$, $Q^5$ and $Y^{L2}$ are as described above, and $Q^6$ is:

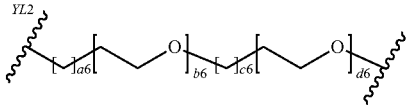

where a6=0 to 5, b6=0 to 16, c6=0 to 5, d6 is 0 to 16, and b6+d6=0 to 16.

a6 is 0 to 5. In some embodiments, a6 is 0. In other embodiments, a6 is 1, 2, 3, 4 or 5.

b6 is 0 to 16. In some embodiments, b6 is 0. In other embodiments, b6 is 1, 2, 3, 4, 5, 6, 7, 8, 9, 10, 11, 12, 13, 14 or 15. In some embodiments, b6 is 0 to 8 or 0 to 4.

c6 is 0 to 5. In some embodiments, c6 is 0. In other embodiments, c6 is 1, 2, 3, 4 or 5.

D6 is 0 to 18. In some embodiments, d2 is 0. In other embodiments, d6 is 1, 2, 3, 4, 5, 6, 7, 8, 9, 10, 11, 12, 13, 14 or 15. In some embodiments, d6 is 0 to 8 or 0 to 4.

b6+d6=0 to 16. In some embodiments, b6+d6=0 to 8 or 0 to 4.

In some embodiments, a6 is 0, b6 is 4, c6 is 1 and d6 is 0.

In other embodiments, b6 is 6, and a6, c6 and d6 are 0.

In other embodiments, all of a6, b6, c6 and d6 are 0, i.e. $Q^6$ is a single bond.

In some embodiments, the second link between X and an active agent may comprise the group -$Q^5$-$Y^{L2}$-$Q^6$-$Q^7$-, where $Q^5$ is connected to X and $Q^7$ is linked to the active agent. In these embodiments, the linker comprises the moiety of formula (IIIg):

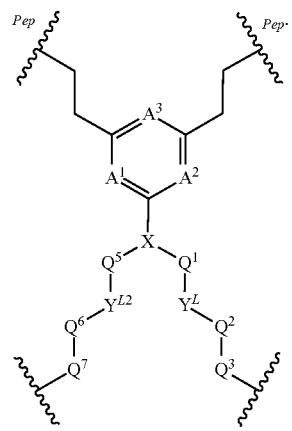

(IIIg)

In these embodiments, the agent-linker is of formula (IIIh):

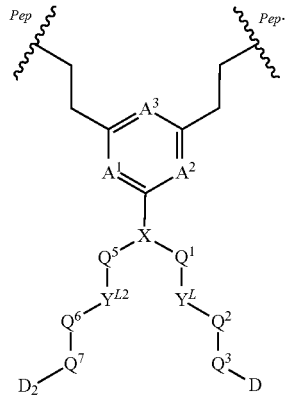
(IIIh)

where D2 is the second active agent.

In these embodiments, the agent-linker comprises the moiety of formula (IIg):

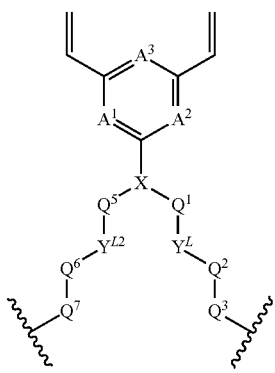
(IIg)

or is of formula (IIh):

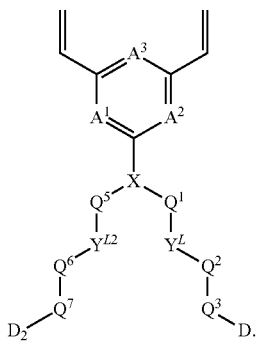
(IIh)

$Q^1$, $Y^L$-, $Q^2$, $Q^3$, $Q^5$, $Y^{L2}$ and $Q^6$ are as described above, and $Q^7$ is:

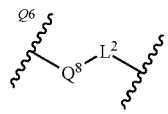

wherein $Q^8$ is a single bond, or

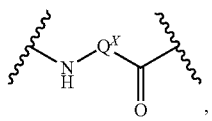

where $Q^X$ is such that $Q^4$ is an amino-acid residue, a dipeptide residue or a tripeptide residue, and L is a group for attachment to the active agent.

In some embodiments, $Q^8$ is a single bond. In some of these embodiments, $Q^6$ may preferably not be a single bond.

In other embodiments, $Q^8$ is

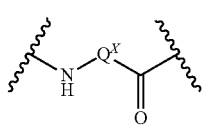

In some of these embodiments, $Q^6$ may be a single bond.

The embodiments of $Q^X$ discussed above apply equally here.

In some embodiments, $L^2$ is selected from:
(a) a single bond;
(b) —C(=O)—;
(c) —NH—; and

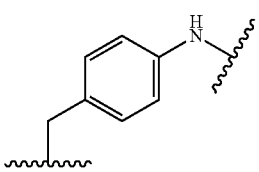
(d)

In some of these embodiments, $L^2$ is a single bond. If $Q^8$ is also a single bond, then $Q^7$ is attached directly to the second active agent.

In other of these embodiments, $L^2$ is —C(=O)— or —NH—.

In other of these embodiments, $L^2$ is

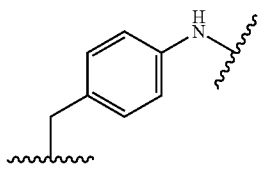

This group can act as a self-immolative group in conjunction with a cleavable linking group.

In some embodiments, the active agents are the same.
In some embodiments, the links to X are the same.

Precursors

The embodiments above apply equally to the precursor compounds of formulae (Ia):

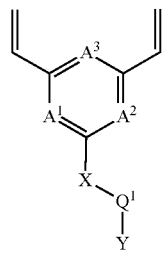

(Ia)

and (Ib):

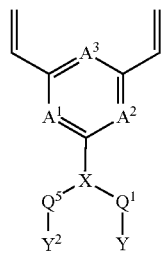

(Ib)

and their precursor, the compounds of formula (Ic):

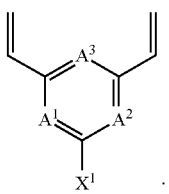

(Ic)

Particular conjugates and compounds of interest as shown in the examples below.

Certain Further Embodiments

In some embodiments of the present invention, the following limitations may be present (whether singly or in any combination, where possible):

$A^1$ and $A^3$ are N

X is O or S

X is N and there are two active agents, each attached to X via a linker $Y^L$ is —C(=O)—NH—

$Y^L$ is

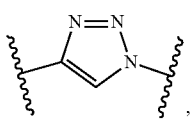

where the N is bound to $Q^1$

In $Q^1$, b1+d1≥1

$Q^2$ is not a single bond $Q^3$ is not a single bond

The cytotoxin is selected from the group comprising auristatins, maytansinoids, tubulysins, calicheamicins, duocarmycins, pyrrolobenzodiazepines (in particular pyrrolobenzodiazepine dimers) and camptothecin analogues.

The antibody or antigen binding fragment thereof is to as tumour-associated antigen The globular protein is albumin Methods of Treatment The conjugates of the present invention where the active agent is a drug may be used in a method of therapy. Also provided is a method of treatment, comprising administering to a subject in need of treatment a therapeutically-effective amount of a conjugate according to the first aspect of the invention, where the active agent is a drug. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a conjugate according to the first aspect of the invention, where the active agent is a drug, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin. Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondylitis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmune disorder is a T cell-mediated immunological disorder.

EXAMPLES

General Experimental Details

Figure 1:
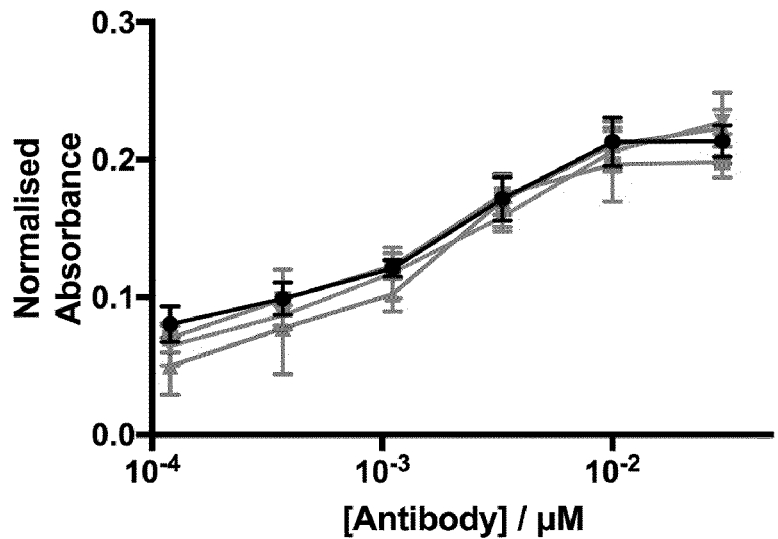
FIG. 1 shows the affinity of three conjugates of linker moieties with trastuzumab to the HER2 receptor, in comparison with unconjugated trastuzumab.

All solvents and reagents were used as received unless otherwise stated. Ethyl acetate, methanol, dichloromethane, acetonitrile and toluene were distilled from calcium hydride. Diethyl ether was distilled from a mixture of lithium aluminium hydride and calcium hydride. Petroleum ether (PE) refers to the fraction between 4° and 60° C. upon distillation. Tetrahydrofuran was dried using Na wire and distilled from a mixture of lithium aluminium hydride and calcium hydride with triphenylmethane as indicator.

Non-aqueous reactions were conducted under a stream of dry nitrogen using oven-dried glassware. Temperatures of 0° C. were maintained using an ice-water bath. Room temperature (rt) refers to ambient temperature.

Yields refer to spectroscopically and chromatographically pure compounds unless otherwise stated. Reactions were monitored by thin layer chromatography (TLC) or liquid chromatography mass spectroscopy (LC-MS). TLC was performed using glass plates pre-coated with Merck silica gel 60 $F_{254}$ and visualized by quenching of UV fluorescence ($\lambda_{max}$=254 nm) or by staining with potassium permanganate. Retention factors ($R_f$) are quoted to 0.01. LC-MS was carried out using a Waters ACQUITY H-Class UPLC with an ESCi Multi-Mode Ionisation Waters SQ Detector 2 spectrometer using MassLynx 4.1 software; EI refers to the electrospray ionisation technique; LC system: solvent A: 2 mM $NH_4OAc$ in $H_2O$/MeCN (95:5); solvent B: MeCN; solvent C: 2% formic acid; column: ACQUITY UPLC® CSH C18 (2.1 mm×50 mm, 1.7 µm, 130 Å) at 40° C.; gradient: 5-95% B with constant 5% C over 1 min at flow rate of 0.6 mL/min; detector: PDA eλ Detector 220-800 nm, interval 1.2 nm.

Flash column chromatography was carried out using slurry-packed Merck 9385 Kieselgel 60 $SiO_2$ (230-400 mesh) under a positive pressure of nitrogen.

Analytical high performance liquid chromatography (HPLC) was performed on Agilent 1260 Infinity machine, using a Supelcosi™ ABZ+PLUS column (150 mm×4.6 mm, 3 µm) with a linear gradient system (solvent A: 0.05% (v/v) TFA in $H_2O$; solvent B: 0.05% (v/v) TFA in MeCN) over 20 min at a flow rate of 1 mL/min, and UV detection ($\lambda_{max}$=220-254 nm).

Melting points (m.p.) were obtained using a BOchi Melting Point B-545 melting point apparatus and are uncorrected.

Infrared (IR) spectra were recorded neat on a Perkin-Elmer Spectrum One spectrometer with internal referencing. Selected absorption maxima ($v_{max}$) are reported in wavenumbers ($cm^{-1}$).

Proton and carbon nuclear magnetic resonance (NMR) were recorded using an internal deuterium lock on Bruker DPX-400 (400 MHz, 101 MHz), Bruker Avance 400 QNP (400 MHz, 101 MHz) and Bruker Avance 500 Cryo Ultrashield (500 MHz, 126 MHz). Tetramethylsilane was used as an internal standard. In proton NMR, chemical shifts (H) are reported in parts per million (ppm), to the nearest 0.01 ppm and are referenced to the residual non-deuterated solvent peak ($CDCl_3$: 7.26, DMSO-$d_6$: 2.50, $CD_3OD$: 3.31, $D_2O$: 4.79). Coupling constants (J) are reported in Hertz (Hz) to the nearest 0.1 Hz. Data are reported as follows: chemical shift, multiplicity (s=singlet; d=doublet; t=triplet; q=quartet; qn=quintet; sep=septet; m=multiplet; or as a combination of these, e.g. dd, dt etc.), integration and coupling constant(s). In carbon NMR, chemical shifts ($\delta_C$) are quoted in ppm, to the nearest 0.1 ppm, and are referenced to the residual non-deuterated solvent peak ($CDCl_3$: 77.16, DMSO-$d_6$, 39.52, $CD_3OD$: 49.00).

High resolution mass spectrometry (HRMS) measurements were recorded with a Micromass Q-TOF mass spectrometer or a Waters LCT Premier Time of Flight mass spectrometer. Mass values are reported within the error limits of ±5 ppm mass units. ESI refers to the electrospray ionisation technique.

Protein LC-MS was performed on a Xevo G2-S TOF mass spectrometer coupled to an Acquity UPLC system using an Acquity UPLC BEH300 C4 column (1.7 µm, 2.1×50 mm). $H_2O$ with 0.1% formic acid (solvent A) and 95% MeCN and 5% water with 0.1% formic acid (solvent B), were used as the mobile phase at a flow rate of 0.2 mL/min. The gradient was programmed as follows: 95% A for 0.93 min, then a gradient to 100% B over 4.28 min, then 100% B for 1.04 minutes, then a gradient to 95% A over 1.04 min. The electrospray source was operated with a capillary voltage of 2.0 kV and a cone voltage of 40 V. Nitrogen was used as the desolvation gas at a total flow of 850 L/h. Total mass spectra were reconstructed from the ion series using the MaxEnt algorithm preinstalled on MassLynx software (v4.1 from Waters) according to the manufacturer's instructions. Trastuzumab samples were deglycosylated with PNGase F (New England Biolabs) prior to LC-MS analysis.

Experiment 1

The following experiments were carried out to identify the potential of a vinyl-heteroaryl scaffold for cysteine re-bridging. It was postulated that vinylpyridine bioconjugation would be too slow to enable efficient cross-linking but that replacement of the pyridine with a pyrimidine would enhance the reactivity to desirable levels by increasing the electron accepting capacity of the heteroaryl ring, without compromising the stability seen with vinylpyridine conjugates.

Synthesis 2-amino-4-vinyl-pyrimidine (1)

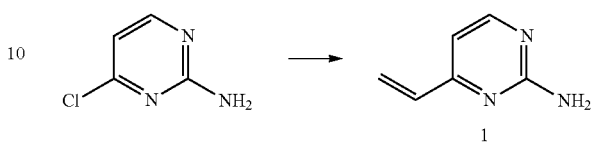

A solution of 2-amino-4-chloropyrimidine (300 mg, 2.32 mmol), potassium vinyltrifluoroborate (931 mg, 6.95 mmol), Pd(dppf)$Cl_2$·$CH_2Cl_2$ (189 mg, 0.232 mmol) and potassium carbonate (1.92 g, 13.9 mmol) in THF/$H_2O$ (10:1, 7.7 mL) was heated to 70° C. for 16 h. Upon completion, the reaction mixture was filtered through Celite® and the solvent removed in vacuo. The resulting residue was purified by flash column chromatography (FCC, 40% EtOAc/PE) to yield 2-amino-4-vinylpyrimidine 1 (195 mg, 1.61 mmol, 70%) as a white solid. $R_f$ 0.12 ($SiO_2$; 40% EtOAc/PE); m.p. 83-86° C.; $v_{max}$ (neat/$cm^{-1}$) 3318, 1648, 1546, 1466, 1403; $\delta_H$ (400 MHz, $CDCl_3$) 8.26 (d, 1H, J=5.2 Hz), 6.65 (d, 1H, J=5.2 Hz), 6.58 (dd, 1H, J=17.4, 10.6 Hz), 6.37 (dd, 1H, J=17.5, 1.3 Hz), 5.64 (dd, 1H, J=10.7, 1.2 Hz), 5.20 (s, 2H); $\delta_C$ (101 MHz, $CDCl_3$) 163.9, 162.7, 158.4, 135.4, 123.0, 108.9; HRMS (ESI) m/z found $[M+H]^+$ 122.0715, $C_6H_8N_3^+$ required 122.0713.

Methyl S-(2-(2-aminopyrimidin-4-yl)ethyl)-N-tert-butoxycarbonyl)-L-cysteinate (3)

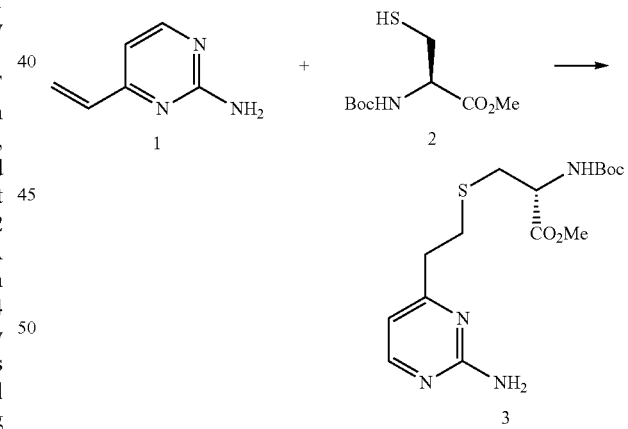

A solution of 1 (15.0 mg, 124 µmol), N-(tert-butoxycarbonyl)-L-cysteine methyl ester (29.2 mg, 124 µmol) in 30% MeCN/sodium phosphate buffer (pH 8, 50 mM, 2.48 mL) was stirred at 37° C. for 15 min. The reaction was analyzed every 2 min by TLC and upon completion, the mixture was diluted with $H_2O$ (10 mL), extracted with EtOAc (4×10 mL), dried (MgSO$_4$) and concentrated in vacuo. The crude residue was purified by FCC (50-100% EtOAc/PE) to yield 3 (39.6 mg, 111 µmol, 90%) as a clear oil. $R_f$ 0.10 ($SiO_2$; 50% EtOAc/PE); $v_{max}$ (neat/$cm^{-1}$) 3334, 2977, 1741, 1704, 1616, 1562, 1457; $\delta_H$ (400 MHz, $CDCl_3$) 8.17 (d, 1H, J=5.1 Hz), 6.49 (d, 1H, J=5.5 Hz), 5.70 (d, 1H, J=7.5 Hz), 5.13 (s, 2H), 4.60-4.56 (m, 1H), 3.74 (s, 3H), 3.03-2.96 (m, 2H), 2.95-2.81 (m, 4H), 1.44 (s, 9H); δ$_C$ (101 MHz, CDCl$_3$) 171.7, 169.3, 163.1, 158.3, 155.4, 111.0, 80.4, 53.7, 52.7, 37.5, 34.7, 30.8, 28.5; HRMS (ESI) m/z found [M+H]$^+$ 357.1606, C$_{15}$H$_{25}$N$_4$O$_4$$^{32}$S$_1$$^+$ required 357.1597.

The conversion of 1 to conjugate 3 was achieved in 15 minutes under bioconjugation compatible conditions.

A competition experiment involving the reaction of 1 with Boc-Cys-OMe and Boc-Lys-OMe at alkaline pH was carried out as follows.

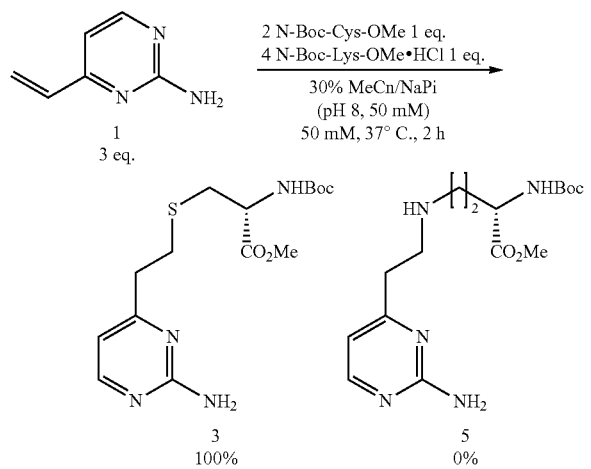

A solution of 2-amino-4-vinylpyrimidine, 1 (12.0 mg, 99.0 μmol), N-(tert-butoxycarbonyl)-L-cysteine methyl ester (7.80 mg, 33.0 μmol) and Nα-(tert-butoxycarbonyl)-L-lysine methyl ester hydrochloride (9.70 mg, 33.0 μmol) in 30% MeCN/sodium phosphate buffer (pH 8, 50 mM, 1.98 mL) was stirred at 37° C. for 2 h.

This experiment showed full conversion to the cysteine conjugate 3. No evidence of the lysine conjugate 5 was observed Comparative Stability In order to compare the stability of the conjugate, the following maleimide derived conjugate (6) was synthesised.

Synthesis of methyl S-(1-benzyl-2,5-dioxopyrrolidin-3-yl)-N-(tert-butoxycarbonyl)-L-cysteinate (6)

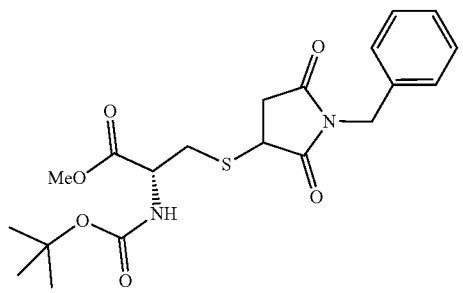 [SMILES: COC(=O)[C@H](CSC1CC(=O)N(Cc2ccccc2)C1=O)NC(=O)OC(C)(C)C]

A solution of N-benzylmaleimide (100 mg, 0.534 mmol), N-(tert-butoxycarbonyl)-L-cysteine methyl ester (151 mg, 0.641 mmol) and triethylamine (74.0 μL, 0.534 mmol) was stirred at 37° C. for 16 h. Upon completion, the reaction mixture was concentrated in vacuo and the crude residue purified by FCC (35% EtOAc/PE) to yield 6 (210 mg, 0.497 mmol, 93%) as a white solid. R$_f$ 0.16 (SiO$_2$; 35% EtOAc/PE); m.p. 73-77° C.; ν$_{max}$ (neat/cm$^{-1}$) 2982, 1744, 1700, 1498, 1434; δ$_H$ (400 MHz, DMSO-d$_6$) 7.39-7.23 (m, 5H), 4.56 (s, 2H), 4.29-4.21 (m, 1H), 4.11-4.07 (m, 1H), 3.64 (s, 3H), 3.28-3.21 (m, 2H), 3.13-3.00 (m, 1H), 2.60-2.52 (m, 1H) 1.38 (s, 9H); δ$_C$ (101 MHz, DMSO-d$_6$) 176.7, 174.9, 171.4, 155.5, 136.0, 128.6, 127.5, 127.4, 78.6, 53.5, 52.2, 41.6, 39.0, 35.9, 32.5, 28.2; HRMS (ESI) m/z found [M+H]$^+$ 423.1576, C$_{20}$H$_{27}$N$_2$O$_6$$^{32}$S$_1$$^+$ required 423.1590.

The stability of conjugate 3 under physiological conditions was investigated by incubation with excess (3 equivalents) reduced L-glutathione (GSH) in pH 7.4 buffer (40% CD$_3$OD/NaPi—50 mM) at 37° C. The stability was tracked via $^1$H NMR and almost no degradation (<5%) was observed after two weeks. In comparison, the corresponding maleimide conjugate 6 showed >50% conversion to the glutathione conjugate after two weeks under the same conditions.

Experiment 2—Linker Synthesis

Synthesis of N-(hex-5-yn-1-yl)-4,6-divinylpyrimidin-2-amine (8)

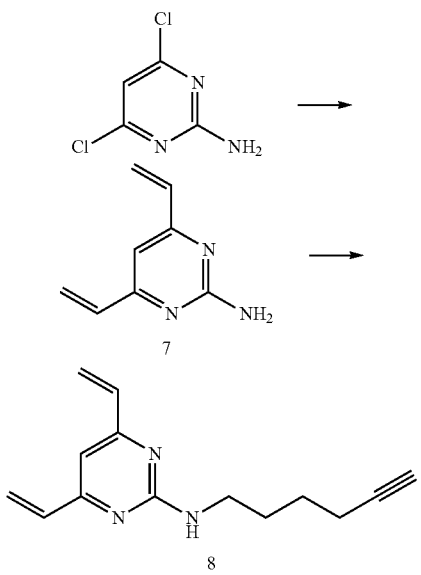

a) 2-amino-4,6-divinylpyrimidine (7)

2-amino-4,6-dichloropyrimidine (200 mg, 1.22 mmol), potassium vinyltrifluoroborate (490 mg, 3.66 mmol), Pd(dppf)Cl$_2$—CH$_2$Cl$_2$ (100 mg, 0.122 mmol) and potassium carbonate (1.01 g, 7.32 mmol) in THF/H$_2$O (10:1, 3.3 mL) were heated to 70° C. for 18 h. Upon completion, the reaction mixture was filtered through Celite® and the solvent removed in vacuo. The resulting residue was purified by FCC (20-40% EtOAc/PE) to yield 2-amino-4,6-divinylpyrimidine 7 (152 mg, 1.03 mmol, 85%) as an off-white solid. R$_f$ 0.29 (SiO$_2$; 50% EtOAc/PE); m.p. 81-83° C.; ν$_{max}$(neat/cm$^{-1}$) 3213, 1567, 1536, 1415; δ$_H$ (500 MHz, DMSO-d$_6$) 6.81 (s, 1H), 6.57 (dd, 2H, J=17.4, 10.6 Hz), 6.54 (s, 2H), 6.32 (dd, 2H, J=17.5, 1.5 Hz), 5.58 (dd, 2H, J=10.7, 1.4 Hz); δ$_C$ (126 MHz, DMSO-d$_6$) 163.6, 163.4, 136.1, 121.5, 104.7; HRMS (ESI) m/z found [M+H]$^+$ 148.0871, C$_8$H$_{10}$N$_3$$^+$ required 148.0869.

b) N-(hex-5-yn-1-yl)-4,6-divinylpyrimidin-2-amine (8)

To a solution of amine 7 (50.0 mg, 0.340 mmol) in DMF (1.5 mL) was added 6-iodo-1-hexyne (223 μL, 1.69 mmol) followed by the slow addition of sodium hydride (60% in mineral oil, 68.0 mg, 1.69 mmol). The reaction mixture was stirred at rt for 15 h, then diluted with H$_2$O (15 mL) and extracted with CH$_2$Cl$_2$ (3×15 mL). The combined organic fractions were washed with brine, dried (MgSO$_4$) and concentrated in vacuo. The crude residue was purified by FCC (20% EtOAc/PE) to yield 8 (40.0 mg, 0.176 mmol, 52%) as a clear oil. R$_f$ 0.36 (SiO$_2$; 25% EtOAc/PE); ν$_{max}$ (neat/cm$^{-1}$) 3298, 2936, 1635, 1539, 1458, 1420; δ$_H$ (500 MHz, CDCl$_3$) 6.58 (dd, 2H, J=17.4, 10.6 Hz), 6.53 (s, 1H), 6.38 (d, 2H, J=17.3 Hz), 5.58 (dd, 2H, J=10.6, 1.4 Hz), 5.29 (s, 1H), 3.51 (q, 2H, J=6.6 Hz), 2.25 (td, 2H, J=10.5, 2.7 Hz), 1.95 (t, 1H, J=2.7 Hz), 1.78-1.72 (m, 2H), 1.67-1.61 (m, 2H); δ$_C$ (126 MHz, CDCl$_3$) 163.7, 162.4, 135.8, 121.9, 105.7, 84.4, 68.7, 41.0, 28.9, 25.9, 18.3; HRMS (ESI) m/z found [M+H]$^+$ 228.1497, C$_{14}$H$_{16}$N$_3$$^+$ required 228.1495.

Synthesis of
N-(4,6-divinylpyrimidin-2-yl)-N-methylglycine (9)

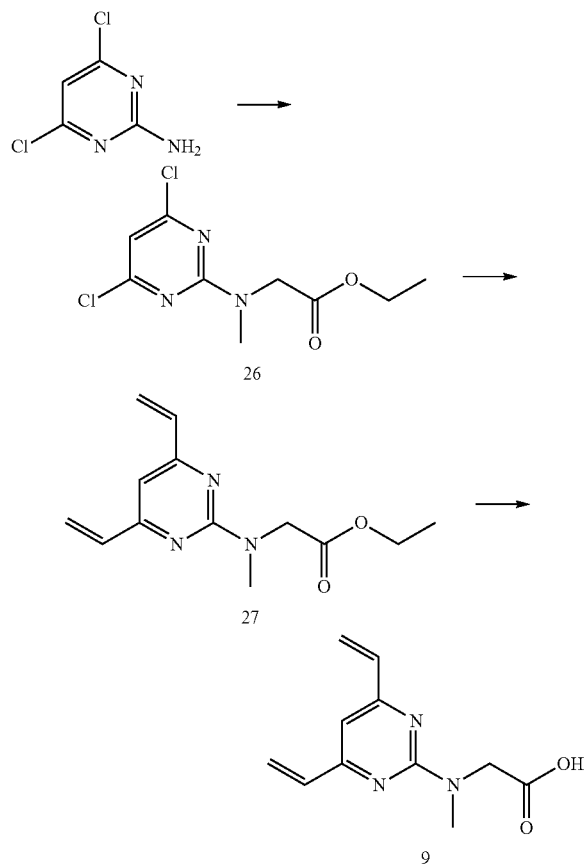

a) Ethyl N-(4,6-dichloropyrimidin-2-yl)-N-methyl-glycinate (26)

To a solution of 2,4,6-trichloropyrimidine (1.00 g, 5.45 mmol) in acetone (6 mL) at 0° C. was added sarcosine ethyl ester hydrochloride (1.01 g, 6.54 mmol) followed by the slow addition of triethylamine (1.90 mL, 13.6 mmol) and the reaction mixture stirred at 0° C. for 90 min. Upon completion, the solvent was removed in vacuo then redissolved in H$_2$O (20 mL) and extracted with CH$_2$Cl$_2$ (4×20 mL). The combined organic fractions were dried (MgSO$_4$), concentrated in vacuo and the crude residue purified by FCC (2-20% EtOAc/PE) to yield 26 (266 mg, 1.01 mmol, 19%) as a clear oil. R$_f$ 0.34 (SiO$_2$; 10% EtOAc/PE); m.p. 40-42° C.; ν$_{max}$ (neat/cm$^{-1}$) 1747, 1567, 1511, 1413, 1198; δ$_H$ (400 MHz, CDCl$_3$) 6.59 (s, 1H), 4.33 (s, 2H), 4.21 (q, 2H, J=7.2 Hz), 3.23 (s, 3H), 1.28 (t, 3H, J=7.2 Hz); δ$_C$ (101 MHz, CDCl$_3$) 169.5, 161.4, 108.8, 61.4, 51.4, 36.8, 14.4; HRMS (ESI) m/z found [M+H]$^+$ 264.0299, C$_9$H$_{12}$Cl$_2$N$_3$O$_2$$^+$ required 264.0307.

Ethyl
N-(4,6-divinylpyrimidin-2-yl)-N-methylglycinate (27)

26 (204 mg, 0.722 mmol), potassium vinyltrifluoroborate (517 mg, 3.86 mmol), Pd(dppf)Cl$_2$·CH$_2$Cl$_2$ (94.6 mg, 0.116 mmol) and potassium carbonate (641 mg, 4.63 mmol) in THF/H$_2$O (10:1, 5.5 mL) were heated to 70° C. for 17 h. Upon completion, the reaction mixture was filtered through Celite® and the solvent removed in vacuo. The resulting residue was purified by FCC (0-4% EtOAc/PE) to yield 27 (182 mg, 0.736 mmol, 95%) as an off-white solid. R$_f$ 0.30 (SiO$_2$; 10% EtOAc/PE); ν$_{max}$ (neat/cm$^{-1}$); 1747, 1560, 1540, 1508, 1401, 1196; δ$_H$ (400 MHz, CDCl$_3$) 6.59 (dd, 2H, J=17.2, 10.5 Hz), 6.49 (s, 1H), 6.38 (d, 2H, J=17.2 Hz), 5.53 (dd, 2H, J=10.5, 1.0 Hz), 4.36 (s, 2H), 4.18 (q, 2H, J=7.1 Hz), 3.32 (s, 3H), 1.23 (t, 3H, J=7.2 Hz); δ$_C$ (101 MHz, CDCl$_3$) 171.1, 162.2, 136.2, 121.3, 105.7, 60.8, 51.8, 36.6, 14.4; HRMS (ESI) m/z found [M+H]$^+$ 248.1397, C$_{13}$H$_{13}$N$_3$O$_2$$^+$ required 248.1399.

c) N-(4,6-divinylpyrimidin-2-yl)-N-methylglycine (9)

To a solution of 27 (40.0 mg, 0.162 mmol) in THF/H$_2$O (1:1, 2 mL) was added LiOH·H$_2$O (14.9 mg, 0.178 mmol) and the reaction mixture stirred at rt for 18 h. Upon completion, the mixture was diluted with H$_2$O (10 mL) and washed with Et$_2$O (10 mL). The aqueous phase was neutralized with 1 M HCl and extracted with CH$_2$Cl$_2$ (4×20 mL). The combined organic fractions were dried (MgSO$_4$) and concentrated in vacuo. The crude residue was triturated with PE to yield 9 (29.0 mg, 0.132 mmol, 82%) as a pale yellow solid. m.p. 92-95° C.; ν$_{max}$ (neat/cm$^{-1}$) 2935, 1705, 1630, 1536, 1395, 1243, 1220; δ$_H$ (400 MHz, CD$_3$OD) 6.67-6.60 (m, 3H), 6.40 (dd, 2H, J=17.4, 1.5 Hz), 5.55 (dd, 2H, J=10.6, 1.5 Hz), 4.36 (s, 2H), 3.28 (s, 3H); δ$_C$ (101 MHz, CDCl$_3$) 174.6, 164.8, 163.4, 137.2, 121.8, 106.1, 52.1, 36.7; HRMS (ESI) m/z found [M+H]$^+$ 220.1087, C$_{11}$H$_{14}$N$_3$O$_2$$^+$ required 220.1086.

Experiment 3

RadA from *Pyrococcus furiosus* is a DNA recombinase enzyme that does not contain any cysteine residues.
Synthetic DNA Production
The synthetic gene of the PfRadA C-terminal ATPase domain containing the desired cysteine mutations was constructed from DNA oligos using overlap-extension PCR. Oligos of approximately 25 bases (Sigma) were designed to include the cysteine mutations. Primers were present in the polymerase chain reaction (PCR) at a concentration of 1 μg/μL. PCR was conducted with Phusion polymerase (Thermo Scientific), and products were purified from agarose gel using a Gel Extraction kit (Qiagen). PCR products and pBAT4 vector were digested using NcoI and XhoI (New England Biolabs) for at least two hours at 37° C., dephosphorylated with Shrimp alkaline phosphatase (SAP) (Agilent Technologies) and gel purified. The gene insert was ligated into plasmid using Quick Ligase Kit (New England Biolabs). The construct was then transformed into DH5a strain E. coli by heat shock at 42° C. Transformants were selected using 100 μg/mL ampicillin in Luria-Bertani (LB) medium. Plasmid was extracted from 2 mL overnight cell cultures using Miniprep Spin kit (Qiagen). The insert was verified by restriction digest analysis and DNA sequencing.

Expression and Purification

The plasmids containing the desired insert were transformed into the BL21(DE3)-pUBS520 strain of E. coli and soluble expression of mutated proteins was confirmed in a small scale expression test. For large scale expression, cells were streaked from previously stored glycerol stocks on ampicillin- and kanamycin-supplemented LB agar plates. Colonies were grown overnight at 37° C. and used to inoculate 1 L cultures of LB media with ampicillin (100 μg/mL) and kanamycin (25 μg/mL). After 4.5 hours incubation at 37° C. ($OD_{600}$=0.7-1.0), cells were induced with IPTG (400 mM). Further incubation at 37° C. was carried out for 3 hours, followed by centrifugation of the cultures. The cell pellet was resuspended in 20 mM MES pH 6.0. Cells were lysed using EmulsiFlex C5 homogeniser (Avestin). The cell lysate was heated to 65° C. for 10 minutes followed by centrifugation. The clarified supernatant was loaded onto a 5 mL HiTrap SP-Sepharose HP column using an AKTA purifier 10 chromatography system. The protein was eluted using ion exchange elution buffer (20 mM MES pH 6.0, 0.5 mM EDTA, 1 M NaCl) gradient of 0-0.5 M NaCl. Appropriate fractions were concentrated to 2 mL using Amico Ultra-4 centrifugal filter units, 10 kDa MWCO (Millipore). One tenth volume of concentrated sample (~180 μL) TCEP was added to each sample and subsequently loaded onto Superdex 75 16/60 gel filtration (GF) column equilibrated with 20 mM MES pH 6.0, 1 mM EDTA, 100 mM NaCl, 0.1 mM TCEP using an AKTA purifier 10 chromatography system. The protein was eluted using GF buffer (20 mM MES pH 6.0, 1 mM EDTA, 100 mM NaCl, 0.1 mM TCEP). Fractions containing purified PfRadA-dCys were concentrated to 2 mL using Amico Ultra-4 centrifugal filter units, 10 kDa MWCO and protein purity analyzed by 15% SDS-PAGE.

Amino acid sequence of PfRadA-dCys, mutations at positions 188 and 344 are highlighted in bold and underlined
ATIGRISTGSKSLDKLLGGGIETQAIT-
EVFGEFGSGKTQLAHTLAVMVQLPPEEGGLNGSVI
WIDTENTFRPERIREIAQCRGLDPDEVLKHIY-
VARAFNSNHQMLLVQQAEDKIKELLNTDRP VKL-
LIVDSLTSHFRSEYIGRGALAERQQKLAKHLADLHR-
LANLYDIAVFVTNQVQANGGHILA
HSATLRVYLRKGKGGKRIARLIDAPHLPEGE-
AVFSITCKGIED Molecular Weight=25,304 Da.
PfRadA-dCys 7 Conjugation To a solution of PfRadA-dCys (10 μL, 2.94 mg/mL) in Tris (25 mM Tris HCl pH 8, 25 mM NaCl, 0.5 mM EDTA, 3 M guanidine hydrochloride) was added TCEP (5 eq.). The mixture was vortexed and incubated at 37° C. for 1 h. A solution of 7 (10 mM in DMSO) was added (15 eq.) and the reaction mixture incubated at 37° C. for 1 h. The excess reagents were removed by repeated diafiltration into PBS using an Amicon-Ultra centrifugal filter (10000 MWCO, Merck Millipore). LC-MS analysis demonstrated >95% conversion to the desired conjugate.

PfRadA-dCys 8 Conjugation

To a solution of PfRadA-dCys (10 μL, 2.94 mg/mL) in Tris (25 mM Tris HCl pH 8, 25 mM NaCl, 0.5 mM EDTA, 3 M guanidine hydrochloride) was added TCEP (5 eq.). The mixture was vortexed and incubated at 37° C. for 1 h. A solution of 8 (10 mM in DMSO) was added (15 eq.) and the reaction mixture incubated at 37° C. for 1 h. The excess reagents were removed by repeated diafiltration into fresh PBS using an Amicon-Ultra centrifugal filter (10000 MWCO, Merck Millipore). LC-MS analysis demonstrated >95% conversion to the desired conjugate.

PfRadA-dCys 9 Conjugation

To a solution of PfRadA-dCys (10 μL, 2.94 mg/mL) in Tris (25 mM Tris HCl pH 8, 25 mM NaCl, 0.5 mM EDTA, 3 M guanidine hydrochloride) was added TCEP (5 eq.). The mixture was vortexed and incubated at 37° C. for 1 h. A solution of 9 (10 mM in DMSO) was added (15 eq.) and the reaction mixture incubated at 37° C. for 1 h. The excess reagents were removed by repeated diafiltration into fresh PBS using an Amicon-Ultra centrifugal filter (10000 MWCO, Merck Millipore). LC-MS analysis demonstrated >95% conversion to the desired conjugate.

Summary

Reduction of the mutant PfRadA with tris(2-carboxyethyl)phosphine hydrochloride (TCEP) followed by the addition of linkers 7, 8 or 9 (15 equiv.) for 1 hour at 37° C. yielded excellent conversion to the desired covalently rebridged conjugates 10, 11 and 12, as detected by LC-MS.

Experiment 4

The bridging reaction was next appraised in a system where interchain bridging between two polypeptide chains would be required. Antibody Fabs (fragment, antigen binding) are heterodimeric proteins where the chains are linked covalently by a single disulfide.

Fab Preparation

Trastuzumab Fab was prepared using the Pierce™ Fab Preparation Kit (ThermoFisher). Briefly, 0.25 mL of immobilized papain was washed with Digestion Buffer containing cysteine-HCl to activate the papain. Trastuzumab (500 μL, 2.95 mg/mL) in Digestion Buffer was added to the immobilized papain and incubated with gentle mixing at 37° C. for 16 h. The digest was isolated from the papain and the Fab purified using a Nab Protein A Plus Spin Column followed by preparative size-exclusion chromatography (25 mM sodium borate pH 8, 100 mM NaCl, 0.5 mM EDTA). The isolated Fab was aliquoted and stored at −20° C. until use.

Trastuzumab Fab 7 Conjugation (13)

To a solution of trastuzumab Fab (10 μL, 27 μM, 1.28 mg/mL) in BBS (25 mM sodium borate pH 8, 25 mM NaCl, 0.5 mM EDTA) was added TCEP (5 eq.). The mixture was vortexed and incubated at 37° C. for 1 h. A solution of 7 (10 mM in DMSO) was added (final concentration of 270 μM, 10 eq.) and the reaction mixture incubated at 37° C. for 1 h. The excess reagents were removed by repeated diafiltration into fresh BBS using an Amicon-Ultra centrifugal filter (10000 MWCO, Merck Millipore). LC-MS analysis demonstrated >95% conversion to the desired conjugate.

Trastuzumab Fab 8 Conjugation (14)

To a solution of trastuzumab Fab (10 μL, 27 μM, 1.28 mg/mL) in BBS (25 mM sodium borate pH 8, 25 mM NaCl, 0.5 mM EDTA) was added TCEP (5 eq.). The mixture was vortexed and incubated at 37° C. for 1 h. A solution of 8 (10 mM in DMSO) was added (final concentration of 270 μM, 10 eq.) and the reaction mixture incubated at 37° C. for 1 h. The excess reagents were removed by repeated diafiltration into fresh BBS using an Amicon-Ultra centrifugal filter (10000 MWCO, Merck Millipore). LC-MS analysis demonstrated >95% conversion to the desired conjugate.

Trastuzumab Fab 9 Conjugation (15)

To a solution of trastuzumab Fab (10 μL, 27 μM, 1.28 mg/mL) in BBS (25 mM sodium borate pH 8, 25 mM NaCl, 0.5 mM EDTA) was added TCEP (5 eq.). The mixture was vortexed and incubated at 37° C. for 1 h. A solution of 9 (10 mM in DMSO) was added (final concentration of 270 μM, 10 eq.) and the reaction mixture incubated at 37° C. for 1 h. The excess reagents were removed by repeated diafiltration into fresh BBS using an Amicon-Ultra centrifugal filter (10000 MWCO, Merck Millipore). LC-MS analysis demonstrated >95% conversion to the desired conjugate.

Trastuzumab Fab 8 Conjugation Kinetic Experiment

To solutions of trastuzumab Fab (5 μL, 51 μM, 2.39 mg/mL) in BBS (25 mM sodium borate pH 8, 25 mM NaCl, 0.5 mM EDTA) was added TCEP (5 eq.). The mixtures were vortexed and incubated at 37° C. for 1 h. A solution of 8 (10 mM in DMSO) was added to each solution (final concentration equal to 10 and 20 equivalents) and the reaction mixture incubated at 37° C. At t=0, 5, 10, 15, 20, 30, 40 and 60 min, 0.5 μL was removed from each reaction, diluted with MilliQ water (9 μL) and quenched with 100 eq. of cysteine (5 mM in DMSO). LC-MS analysis was then used to quantify conversion.

Cysteine Selectivity

To a solution of trastuzumab Fab (5 μL, 29.6 μM, 1.41 mg/mL) in BBS (25 mM sodium borate pH 8, 25 mM NaCl, 0.5 mM EDTA) was added solution of 8 (10 mM in DMSO, final concentration of 296 μM, 10 eq.). The reaction mixture was vortexed and incubated at 37° C. for 2 h. LC-MS analysis revealed that no reaction had occurred.

Summary

Evaluation of the DVP linker platform by reaction of reduced trastuzumab Fab with 7, 8 or 9 led to complete conversion to the desired interchain-bridged conjugates 13-15 in ~30 minutes using a slight excess of the linker (10 equiv.).

Kinetic analysis of the bridging rate of 8 was also conducted with 10 and 20 equivalents of linker. Strikingly, >90% re-bridging of the Fab chains was observed for both stoichiometries after only 15 minutes. To confirm the selectivity of the DVP linker platform for cysteine residues, 8 was incubated with unreduced trastuzumab Fab and no reaction was observed after two hours at 37° C.

Experiment 5

The linkers of the present invention enable modification of all four interchain disulfides in an IgG, generating an ADC with definitive modification sites while giving a consistent DAR of four.

Trastuzumab 7 Conjugation (16)

To a solution of trastuzumab (10 μL, 17 μM, 2.5 mg/mL) in Tris (25 mM Tris HCl pH 8, 25 mM NaCl, 0.5 mM EDTA) was added TCEP (10 eq.). The mixture was vortexed and incubated at 37° C. for 1 h. A solution of 7 (10 mM in DMSO) was added (final concentration of 680 μM, 40 eq.) and the reaction mixture incubated at 37° C. for 2 h. The excess reagents were removed by repeated diafiltration into PBS using an Amicon-Ultra centrifugal filter (10000 MWCO, Merck Millipore). LC-MS and SDS-PAGE analysis demonstrated >95% conversion to the bridged conjugate.

Trastuzumab 8 Conjugation (17)

To a solution of trastuzumab (50 μL, 22.7 μM, 3.34 mg/mL) in Tris (25 mM Tris HCl pH 8, 25 mM NaCl, 0.5 mM EDTA) was added TCEP (10 eq.). The mixture was vortexed and incubated at 37° C. for 1 h. A solution of 8 (10 mM in DMSO) was added (final concentration of 908 μM, 40 eq.) and the reaction mixture incubated at 37° C. for 2 h. The excess reagents were removed by repeated diafiltration into PBS using an Amicon-Ultra centrifugal filter (10000 MWCO, Merck Millipore). LC-MS, SDS-PAGE and RP-HPLC analysis demonstrated >95% conversion to the bridged conjugate.

Trastuzumab 9 Conjugation (18)

To a solution of trastuzumab (10 μL, 17 μM, 2.5 mg/mL) in Tris (25 mM Tris HCl pH 8, 25 mM NaCl, 0.5 mM EDTA) was added TCEP (10 eq.). The mixture was vortexed and incubated at 37° C. for 1 h. A solution of 9 (10 mM in DMSO) was added (final concentration of 680 μM, 40 eq.) and the reaction mixture incubated at 37° C. for 2 h. The excess reagents were removed by repeated diafiltration into PBS using an Amicon-Ultra centrifugal filter (10000 MWCO, Merck Millipore). LC-MS and SDS-PAGE analysis demonstrated >95% conversion to the bridged conjugate.

Summary

The fully re-bridged mAbs 16, 17 and 18 were evident by LC-MS, suggesting good conversion to the desired bioconjugates. Analysis by SDS-PAGE and RP-HPLC confirmed the presence of the correctly bridged antibodies along with the 'half-antibody' formed by intrachain bridging of the hinge region heavy chain cysteines.

To determine the effect of bridging on mAb aggregation, antibody conjugate 18 was analyzed by size-exclusion chromatography (SEC). Identical aggregation levels were observed for 18 and the unmodified mAb.

Trastuzumab-DVP 18 Stability

A solution of trastuzumab-DVP, 18 (10 μL, 14 μM, 2.10 mg/mL) in PBS was diluted with 10 μL of reconstituted human plasma (Sigma) and 80 μL of PBS. To this solution was added reduced L-glutathione (final concentration=1 μM) and mixture incubated at 37° C. for 14 days. Aliquots were removed after 0, 1, 3, 5, 7, 9, 11 and 14 days, flash frozen and stored at −20° C. until analysis. LC-MS and SDS-PAGE analysis revealed full stability of the conjugate after two weeks.

Conclusion

The synthesis of these conjugates demonstrates the utility of the DVP platform to efficiently generate a highly stable modified antibody in a site-selective manner.

Experiment 6

Dox-PEG$_4$-N$_3$ (19)

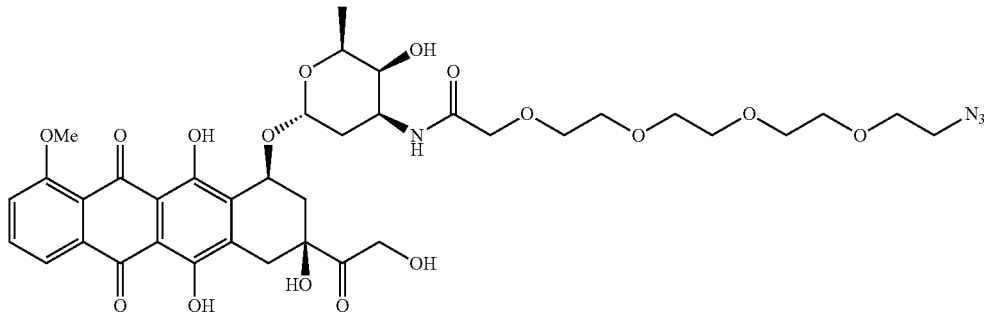 [SMILES: COc1cccc2c1C(=O)c1c(O)c3c(c(O)c1C2=O)C[C@@](O)(C(=O)CO)C[C@@H]3O[C@H]1C[C@H](NC(=O)COCCOCCOCCOCCN=[N+]=[N-])[C@H](O)[C@H](C)O1]

To a solution of doxorubicin hydrochloride (10.9 mg, 20.0 μmol) in DMF (1.10 mL) was added DIPEA (7.00 μL, 40.0 μmol) followed by HBTU (9.10 mg, 24.0 μmol). The mixture was stirred at rt for 5 min. 14-azido-3,6,9,12-tetraoxa-tetradecanoic acid (0.5 M in TBME, 44.5 μL, 20.0 mmol) was added and the mixture stirred for 2.5 h. Upon completion, the reaction mixture was diluted with H$_2$O (10 mL) and the product extracted in CH$_2$Cl$_2$ (4×10 mL), dried (MgSO$_4$). The organic fractions were concentrated and the crude residue purified by FCC (5% MeOH/EtOAc) to yield 19 (10.9 mg, 13.6 μmol, 65%) as a clear oil. R$_f$ 0.22 (SiO$_2$; 10% MeOH/CH$_2$Cl$_2$); v$_{max}$ (neat/cm$^{-1}$) 2922, 2106, 1724, 1654, 1619, 1578, 1535, 1411; δ$_H$ (500 MHz, CDCl$_3$) 8.04 (d, 1H, J=7.8 Hz), 7.78 (t, 1H, J=8.1 Hz), 7.39 (d, 1H, J=8.0 Hz), 5.51 (d, 1H, J=3.8 Hz), 5.30-5.29 (m, 1H), 4.77 (d, 2H, J=3.1 Hz), 4.61 (s, 1H), 4.22-4.16 (m, 1H), 4.13 (q, 1H, J=6.5 Hz), 4.08 (s, 3H), 3.93 (m, 2H), 3.72-3.63 (m, 15H), 3.40 (t, 2H, J=5.0 Hz), 3.28 (dd, 1H, J=18.8, 1.7 Hz), 3.04 (s, 1H), 2.37 (d, 1H, J=14.7 Hz), 2.16 (dd, 1H, J=14.7, 4.0 Hz), 1.93 (td, 1H, J=19.8, 4.2 Hz), 1.80 (dd, 1H, J=13.4, 5.0 Hz), 1.29 (d, 3H, J=6.6 Hz); δ$_C$ (126 MHz, CDCl$_3$) 214.1, 187.3, 186.9, 169.4, 161.2, 156.4, 155.9, 135.9, 135.7, 133.8, 133.8, 121.1, 120.0, 118.6, 111.7, 111.5, 101.1, 76.8, 71.1, 70.9, 70.7, 70.6, 70.6, 70.4, 70.2, 70.2, 69.8, 69.3, 67.6, 65.7, 56.8, 50.8, 45.0, 35.8, 34.1, 29.8, 17.1; HRMS (ESI) m/z found [M+H]$^+$ 803.2968, C$_{37}$H$_{47}$N$_4$O$_{16}^+$ required 803.2982.

Trastuzumab-DVP Dox-PEG$_4$-N$_3$ CuAAC (21)

To a solution of trastuzumab-DVP 18 (70 μL, 12.5 μM, 1.86 mg/mL) in PBS was added 19 (5 mM in DMSO, to 150 μM), CuSO$_4$·5H$_2$O (to 250 μM), THPTA (to 1.25 mM) and sodium ascorbate (to 1.88 mM). The mixture was vortexed and incubated at 37° C. for 2 h. The excess reagents were removed by repeated diafiltration into PBS using an Amicon-Ultra centrifugal filter (10000 MWCO, Merck Millipore). LC-MS and UV-vis analysis revealed conversion to an ADC with an average DAR of 4.0.

Trastuzumab-DVP AlexaFluor488 Azide CuAAC (22)

To a solution of trastuzumab-DVP 18 (55 μL, 13.7 μM, 2.05 mg/mL) in PBS was added AlexaFluor-488 Azide (ThermoFisher) (5 mM in DMSO, final concentration of 164.4 μM), CuSO$_4$·5H$_2$O (final concentration of 274 μM), THPTA (final concentration of 1.37 mM) and sodium ascorbate (final concentration of 2.06 mM). The mixture was vortexed and incubated at 37° C. for 4 h. The excess reagents were removed by repeated diafiltration into PBS using an Amicon-Ultra centrifugal filter (10000 MWCO, Merck Millipore). LC-MS and UV-vis analysis revealed conversion to an antibody-fluorophore conjugate (AFC) with an average fluorophore-antibody ratio (FAR) of 3.89.

N$_3$—PEG$_4$-MMAE (23)

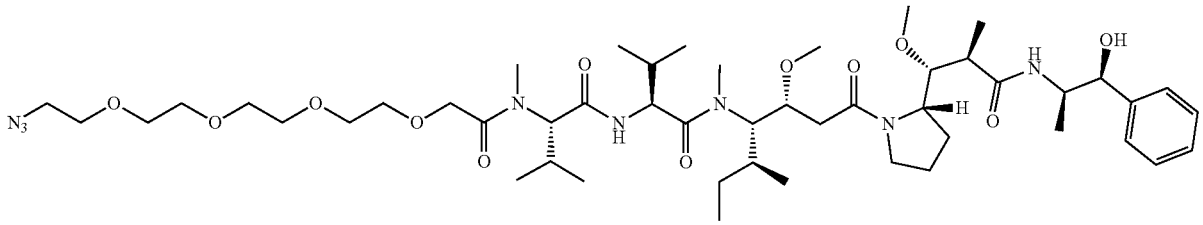 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)COCCOCCOCCOCCN=[N+]=[N-])C(C)C]

A solution of N$_3$-PEG$_4$-COOH (50.0 μL, 25.1 μmol, 0.5 M in TBME, 90%), HBTU (12.7 mg, 33.4 μmol) and DIPEA (17.5 μL, 100 μmol) in DMF (0.5 mL) was stirred at rt for 15 min. To this was added a solution of MMAE (12.0 mg, 16.7 μmol) in DMF (0.5 mL) and the reaction mixture stirred at rt for 18 h. Upon completion, the solvent was removed under a stream of N$_2$ and the crude residue was purified by FCC (0-5% MeOH/CH$_2$Cl$_2$) to yield 23 (14.6 mg, 14.9 μmol, 90%) as a clear oil. R$_f$ 0.48 (SiO$_2$; 10% MeOH/CH$_2$Cl$_2$); v$_{max}$ (neat/cm$^{-1}$) 3423, 2926, 2109, 1629, 1454, 1098; HPLC (5-95% MeCN/H$_2$O over 20 min) retention time 11.097 min; HRMS (ESI) m/z found [M+Na]$^+$ 999.6100, C$_{49}$H$_{84}$N$_8$O$_{12}$Na$_1^+$ required 999.6100.

DVP-PEG$_4$-MMAE (24)

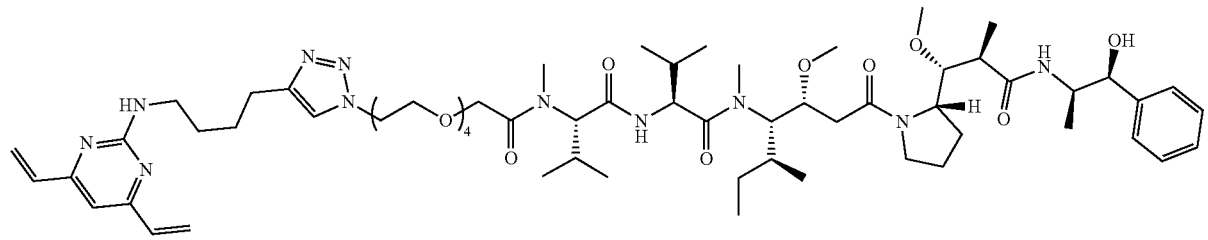

To a degassed solution of 23 (4.90 mg, 5.00 μmol) and 9 (2.30 mg, 10.0 μmol) in CH$_2$Cl$_2$ (0.25 mL) was added a degassed solution of CuSO$_4$·5H$_2$O (1.50 mg, 6.00 μmol), THPTA (4.40 mg, 10.0 μmol) and sodium ascorbate (5.00 mg, 25.0 μmol) in H$_2$O/$^t$BuOH (0.5 mL, 1:1) and the reaction mixture stirred at rt for 2 h. Upon completion, the reaction was diluted with H$_2$O (15 mL) and extracted with CH$_2$Cl$_2$ (5×15 mL). The combined organic fractions were dried (MgSO$_4$), concentrated in vacuo and the crude residue purified by FCC (0-10% MeOH/CH$_2$Cl$_2$) to yield 24 (1.80 mg, 1.50 μmol, 30%) as a clear oil. R$_f$ 0.28 (SiO$_2$; 7.5% MeOH/CH$_2$Cl$_2$); v$_{max}$ (neat/cm$^{-1}$) 3301, 2926, 1632, 1544, 1452, 1098; HPLC (5-95% MeCN/H$_2$O over 20 min) retention time 10.309 min; HRMS (ESI) m/z found [M+Na]+ 1226.7502, C$_{63}$H$_{101}$N$_{11}$O$_{12}$Na$_1^+$ required 1226.7523.

Trastuzumab DVP-PEG4-MMAE Conjugation (25)

To a solution of trastuzumab (30 μL, 25.5 μM, 3.81 mg/mL) in Tris (25 mM Tris HCl pH 8, 25 mM NaCl, 0.5 mM EDTA) was added TCEP (10 eq.). The mixture was vortexed and incubated at 37° C. for 1 h. A solution of 24 (10 mM in DMSO) was added (final concentration of 1.02 mM, 40 eq.) and the reaction mixture incubated at 37° C. for 3 h. The excess reagents were removed by repeated diafiltration into PBS using an Amicon-Ultra centrifugal filter (10000 MWCO, Merck Millipore). LC-MS and SDS-PAGE analysis demonstrated >95% conversion to the half-antibody conjugate.

Experiment 7

The biological effects of DVP-bridging were then investigated.

Enzyme-Linked Immunosorbent Assay (ELISA)

A 96-well plate was coated with 100 μL of a 0.25 μg/mL solution of HER2 (Sino Biological, His-tagged) overnight at 4° C. Coating solutions were removed and each well washed with PBS (2×200 μL). Each well was then blocked with 1% BSA in PBS (200 μL) for 1 h at room temperature. The blocking solution was then removed and each well washed with PBS (3×200 μL). Wells were treated with a serial dilution of trastuzumab and trastuzumab-DVP conjugates 16, 17 and 18 in PBS (100 μL of 30 nM, 10 nM, 3.33 nM, 1.11 nM, 0.37 nM, 0.12 nM, 0 nM) and incubated at room temperature for 2 h. The conjugate solutions were removed and each well was washed with 0.1% Tween 20 in PBS (2×200 μL) followed by PBS (3×200 μL). Next, 100 μL of detection antibody (1:1000 dilution of a mouse anti-human IgG-HRP, ThermoFisher) in PBS was added to each well and incubated at room temperature for 1 h. Each well was washed with 0.1% Tween 20 in PBS (2×200 μL) followed by PBS (3×200 μL). Finally, an OPD solution (100 μL of a solution prepared by dissolving 1 capsule in 9 mL H$_2$O and 1 mL stable peroxide substrate buffer (10×), ThermoFisher) was added to each well. After 10-15 minutes, 4M HCl$_{(aq)}$ (50 μL) was added to each well to quench the reaction. Absorbance was measured at 490 nm and 590 nm. Measurements were performed in quadruplicate and three independent repeats were performed.

The results are shown in FIG. 1, which shows that 16-18 all demonstrated comparable affinities to the native antibody for the HER2 receptor. In FIG. 1:
● Tratuzumab
■ 16
▲ 17
▼ 18

Cells Lines

HER2-positive SKBR3 and BT474 cells were obtained from the American Type Culture Collection (ATCC) and HER2-negative MCF7 and T47D cells were obtained from the European Collection of Authenticated Cell Cultures (ECACC) and ATCC, respectively. SKBR3 cells were maintained in high glucose McCoy's 5A medium, supplemented with 10% heat-inactivated foetal-bovine serum (FBS), 50 U/mL penicillin and 50 μg/mL streptomycin. MCF7 cells were maintained in Dulbecco's Modified Eagle Medium (DMEM) supplemented with 10% heat-inactivated fetal-bovine serum (FBS), 2 mM L-glutamine, 50 U/mL penicillin and 50 μg/mL streptomycin. BT474 and T47D cell lines were maintained in RPM11640 medium supplemented with 10% heat-inactivated fetal-bovine serum (FBS), 2 mM L-glutamine, 50 U/mL penicillin and 50 μg/mL streptomycin. All cell lines were incubated at 37° C. with 5% CO$_2$.

Live Cell Labeling/Internalization by Fluorescence-Activated Cell Sorting (FACS)

SKBR3, BT474, MCF7 and T47D cell lines were seeded in 6-well plates at 10$^6$ cells/well and allowed to adhere for 24 h at 37° C. with 5% CO$_2$. Cells were treated with 50 nM 22, AlexaFluor™488 azide or PBS in complete growth medium for 1 h at 37° C. Next, growth medium was removed, the cells were washed with PBS to remove unbound antibodies and the cells were detached with Accutase® cell dissociation reagent (StemPro), washed with PBS, pelleted and resuspended in PBS (100 μL). Analysis was conducted on an Amnis® ImageStream® imaging flow cytometer (Merck Millipore). DRAQ5™ (ThermoFisher) was used as a nuclear stain.

Analysis revealed full labelling of both HER2-positive cell lines while only minor labelling was observed with HER2-negative cell lines. Internalization of the conjugate was observed in both HER2-positive cell types, with no internalization visible in either HER2-negative cell line, confirming that DVP bridging does not affect receptor specificity, affinity or complex internalization.

Cell Viability

Cells were seeded in 96-well plates for 24 h at 37° C. with 5% CO$_2$. SKBR3 cells were seeded at 15,000 cells/well, BT474 cells were seeded at 20,000 cells/well, MCF7 cells were seeded at 7,500 cells/well and T47D cells were seeded at 10,000 cells/well. Serial dilutions of 25, trastuzumab and MMAE were added to the cells in complete growth medium and incubated at 37° C. with 5% $CO_2$ for 96 h. Cell viability was measured using CellTiter-Glo viability assay (Promega) according to the manufacturer's instructions. Cell viability was plotted as a percentage of untreated cells. Each measurement was taken in triplicate and three independent repeats were performed.

Cell Growth Assay

Cells were seeded in 96-well plates for 24 h at 37° C. with 5% $CO_2$. SKBR3 cells were seeded at 15,000 cells/well, BT474 cells were seeded at 20,000 cells/well, MCF7 cells were seeded at 7,500 cells/well and T47D cells were seeded at 10,000 cells/well. Serial dilutions of 25 were added to the cells in complete growth medium and incubated at 37° C. with 5% $CO_2$ for 6 days in an IncuCyte®. Cell growth is given as percentage confluence. Each concentration was measured in triplicate and error bars indicate standard deviation.

Cytotoxicity was only observed in the HER2-positive cell lines (FIG. 2a), demonstrating that DVP linkers do not affect the cell-killing ability of MMAE, enabling the use of these linkers for the delivery of auristatin payloads with non-cleavable linkers. In contrast to the specific cytotoxicity observed with our ADC, treatment of the same cell lines with free MMAE resulted in high levels of cytotoxicity in both HER2-positive and HER2-negative cell lines (FIG. 2b). Furthermore, incubation of unmodified trastuzumab with these cell lines did not cause significant cytotoxicity (FIG. 2c).

Figure 2A:
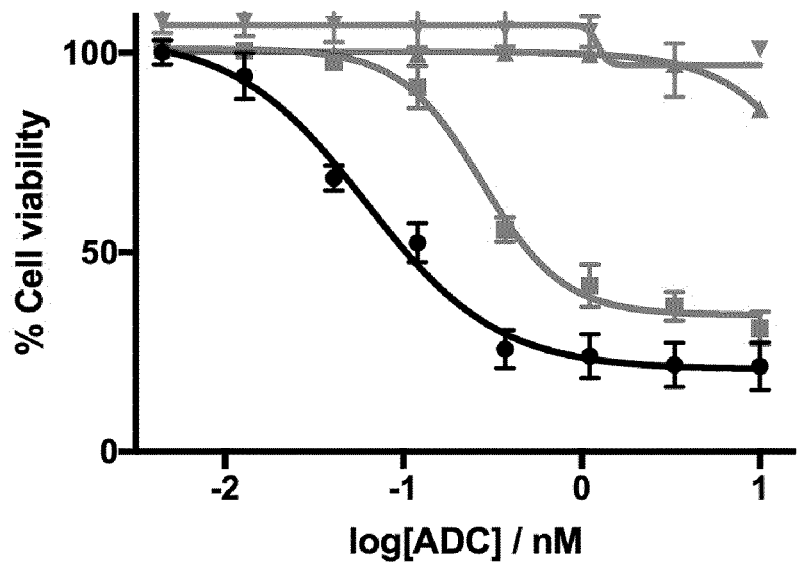
FIGS. 2a, 2b and 2c show the cell viability of four cell lines when treated with conjugates of the invention.
Figure 2B:
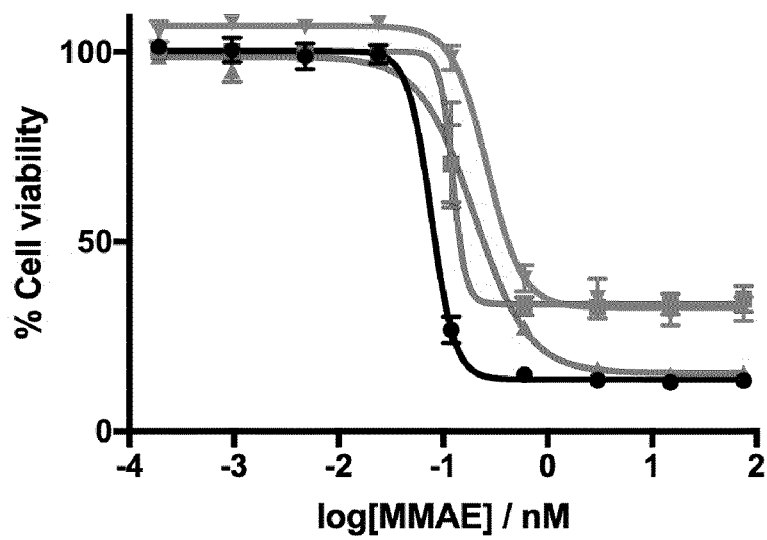
Figure 2C:
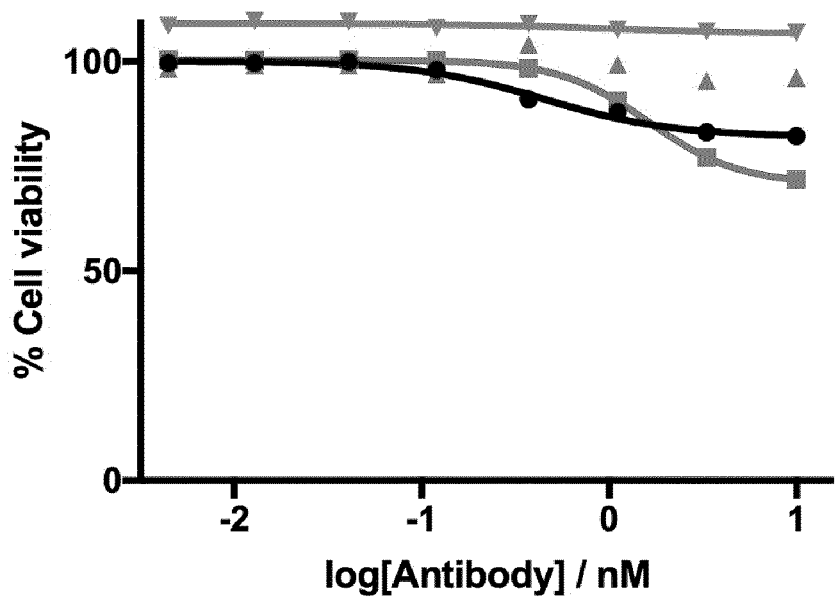

In FIGS. 2a, 2b and 2c:
- ● SKBR3
- ■ BT474
- ▲ MCF7
- ▼ T47D

Experiment 8

Synthesis of 4-((4,6-divinylpyrimidin-2-yl)amino)butanoic acid (30)

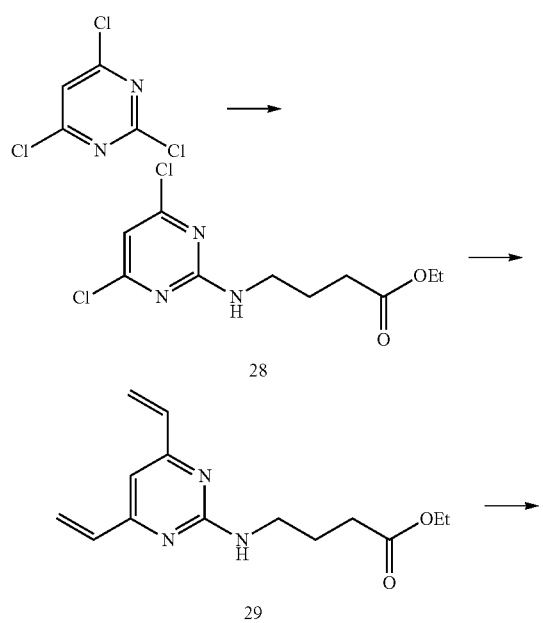

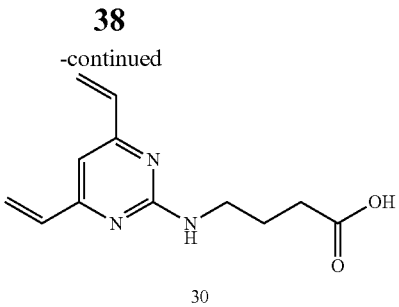

a) Ethyl 4-((4,6-dichloropyrimidin-2-yl)amino)butanoate (28)

A solution of 2,4,6-trichloropyrimidine (1.00 g, 5.45 mmol), ethyl 4-aminobutyrate hydrochloride (1.10 g, 6.54 mmol) and triethylamine (1.90 mL, 13.63 mmol) in acetone was stirred at 0° C. for 2 h. Upon completion, the reaction was concentrated in vacuo and the residue redissolved in $H_2O$ (20 mL) and $CH_2Cl_2$ (20 mL). The layers were separated and the aqueous phase was extracted with further $CH_2Cl_2$ (3×20 mL). The combined organic fractions were dried ($MgSO_4$), concentrated in vacuo and the crude residue purified by FCC (5-30% EtOAc/PE) to yield ethyl 4-((4,6-dichloropyrimidin-2-yl)amino)butanoate (420 mg, 1.51 mmol, 28%) as a white solid.

b) Ethyl 4-((4,6-divinylpyrimidin-2-yl)amino)butanoate (29)

A solution of ethyl 4-((4,6-dichloropyrimidin-2-yl)amino)butanoate 28 (200 mg, 0.719 mmol), potassium vinyltrifluoroborate (482 mg, 3.60 mmol), Pd(dppf)$Cl_2$·$CH_2Cl_2$ (88.1 mg, 0.108 mmol) and potassium carbonate (596 mg, 4.31 mmol) in THF/$H_2O$ (10:1, 5.5 mL) was heated to 70° C. for 15 h. Upon completion, the reaction mixture was filtered through Celite® and the solvent removed in vacuo. The resulting residue was purified by flash column chromatography (FCC, 20% EtOAc/PE) to yield ethyl 4-((4,6-divinylpyrimidin-2-yl)amino)butanoate (181 mg, 0.693 mmol, 96%) as a pale yellow oil.

c) 4-((4,6-divinylpyrimidin-2-yl)amino)butanoic acid (30)

A solution of ethyl 4-((4,6-divinylpyrimidin-2-yl)amino) butanoate 29 (160 mg, 0.612 mmol) and LiOH·$H_2O$ (56.6 mg, 1.35 mmol) in THF/$H_2O$ (6 mL, 1:1) was stirred at rt for 21 h. Upon completion, the reaction was diluted with $H_2O$ (10 mL) and washed with $Et_2O$ (15 mL) and concentrated in vacuo. The residue was suspended in MeOH, filtered and the filtrate concentrated in vacuo to yield 4-((4,6-divinylpyrimidin-2-yl)amino)butanoic acid (138 mg, 0.592 mmol, 97%) as a pale yellow solid.

Synthesis of DVP-Val-Cit-PABC-MMAE (36)
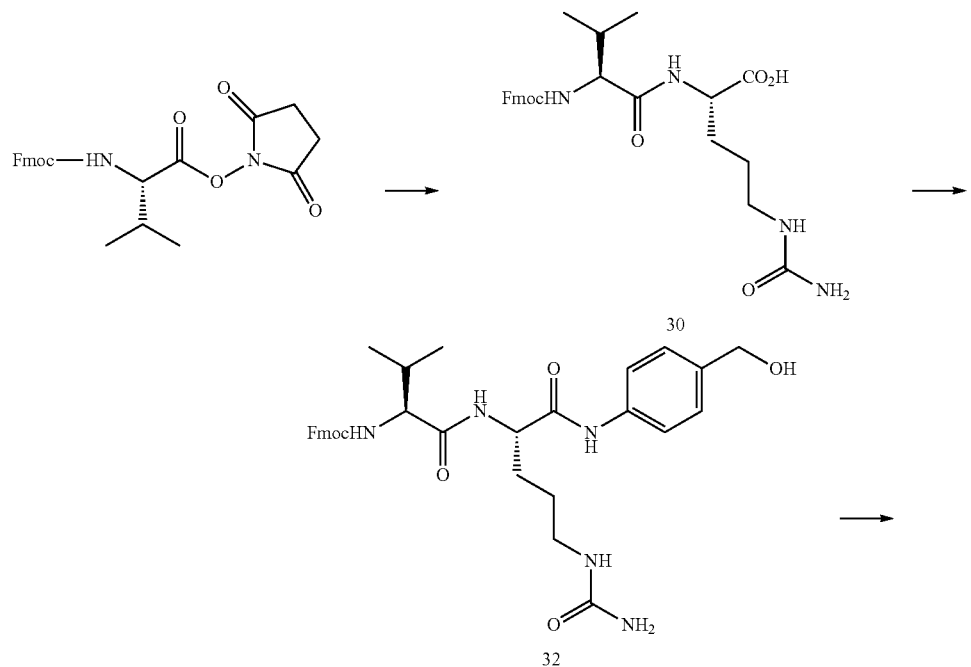
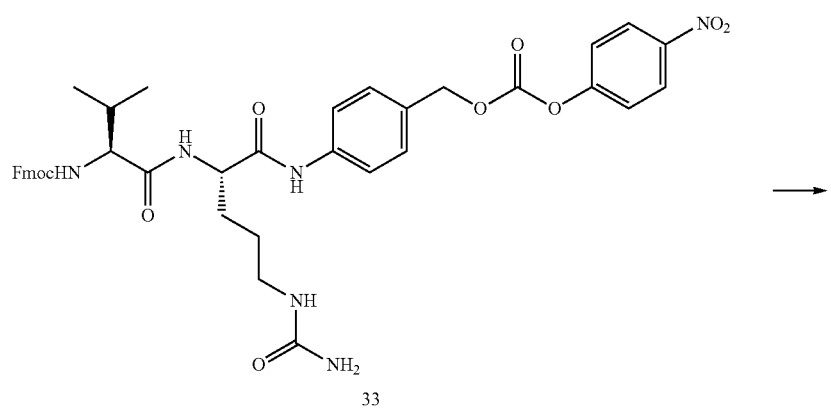
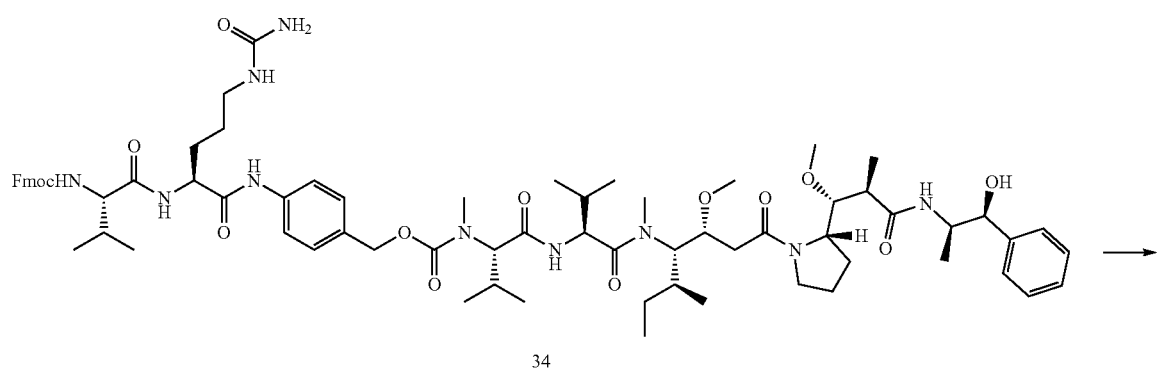

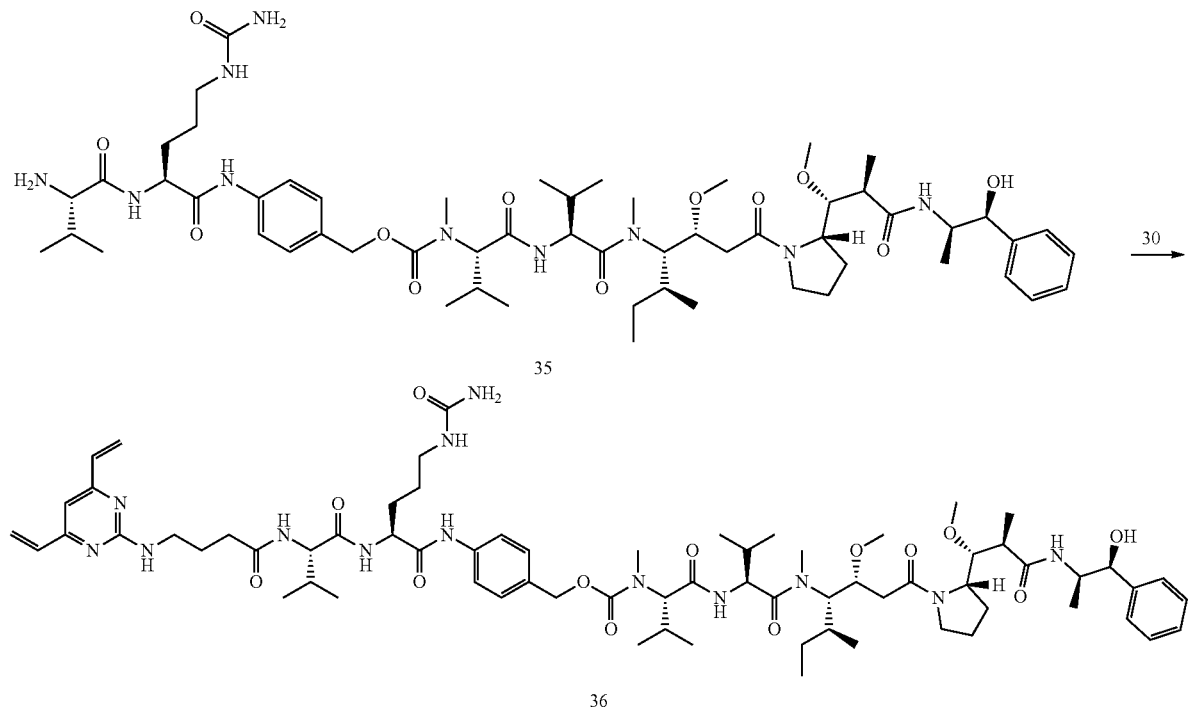

a) Fmoc-Val-Cit-OH (31)

To a solution of Fmoc-Val-OSu (1.00 g, 2.29 mmol) and NaHCO₃ (260 mg, 3.09 mmol) in H₂O (7.5 mL) at 0° C. was added a solution of L-citrulline (501 mg, 2.87 mmol) in DME (7.5 mL). THF (4 mL) was added, the reaction warmed to rt and stirred for 28 h. Upon completion, the reaction was adjusted to pH 10 with saturated aqueous K₂CO₃ and washed with EtOAc (2×50 mL). The aqueous layer was acidified to pH 4 with 15% aqueous citric acid and the formed gelatinous mixture was filtered. The wet cake was redissolved in THF/MeOH (50 mL), TBME (100 mL) was added and the mixture was stirred at rt for 16 h. The mixture was filtered and the filtrate concentrated in vacuo to yield Fmoc-Val-Cit-OH (1.12 g, 2.25 mmol, 98%) as an off-white solid.

b) Fmoc-Val-Cit-PABA (32)

A solution of Fmoc-Val-Cit-OH 31 (600 mg, 1.21 mmol), 4-aminobenzyl alcohol (298 mg, 2.42 mmol) and 2-Ethoxy-1-ethoxycarbonyl-1,2-dihydroquinoline (598 mg, 2.42 mmol) in CH₂Cl₂/MeOH (12.6 mL, 2:1) was stirred at rt for 15 h. Upon completion, the mixture was diluted with Et₂O (30 mL), sonicated briefly, filtered and washed with Et₂O to yield Fmoc-Val-Cit-PABC (428 mg, 0.710 mmol, 59%) as an off-white solid.

c) Fmoc-Val-Cit-PAB-PNP (33)

A solution of Fmoc-Val-Cit-PABA 32 (200 mg, 0.332 mmol), bis(4-nitrophenyl) carbonate (202 mg, 0.665 mmol) and DIPEA (86.8 μL, 0.498 mmol) was stirred at rt for 3 h. Upon completion, the mixture was concentrated under a stream of N₂. The crude residue was precipitated with EtOAc (3 mL) and Et₂O (30 mL), allowed to stand for 30 min and then filtered to yield Fmoc-Val-Cit-PAB-PNP (210 mg, 0.274 mmol, 83%) as a light brown solid.

d) Fmoc-Val-Cit-PABC-MMAE (34) A solution of MMAE (25.0 mg, 34.8 μmol), Fmoc-Val-Cit-PAB-PNP 33 (53.4 mg, 69.6 μmol), 1-hydroxybenzotriazole hydrate (9.40 mg, 69.6 μmol) and pyridine (28.2 μL, 348 μmol) in DMF (1.5 mL) was stirred at rt for 17 h. Upon completion, the reaction mixture was concentrated under a stream of N₂. The crude residue was dissolved in CH₂Cl₂/MeOH (30 mL, 3:2), filtered and the filtrate purified by FCC (0-10% MeOH/CH₂Cl₂) to yield Fmoc-Val-Cit-PABC-MMAE (22.0 mg, 16.4 μmol, 47%) as a clear oil.

e) H-Val-Cit-PABC-MMAE (35)

A solution of Fmoc-Val-Cit-PABC-MMAE 34 (20.0 mg, 14.9 μmol) and piperidine (7.40 μL, 74.3 μmol) in DMF (1 mL) was stirred at rt for 1 h. Upon completion, the reaction mixture was concentrated under a stream of N₂ and carried forward without further purification.

f) DVP-Val-Cit-PABC-MMAE (36)

A solution of H-Val-Cit-PABC-MMAE 33 (5.00 mg, 4.45 μmol), 4-((4,6-divinylpyrimidin-2-yl)amino)butanoic acid 30 (2.60 mg, 11.1 μmol), HBTU (3.40 mg, 8.90 μmol), 1-hydroxybenzotriazole hydrate (1.20 mg, 8.90 μmol) and DIPEA (3.90 μL, 22.3 μmol) in DMF (1 mL) was stirred at rt for 14 h. Upon completion, the reaction was concentrated under a stream of N₂ and the crude residue purified by preparative HPLC to yield DVP-Val-Cit-PABC-MMAE (1.2 mg, 0.896 μmol, 20%) as a white solid.

Synthesis of DVP-Val-Ala-PABC-MMAE (40)

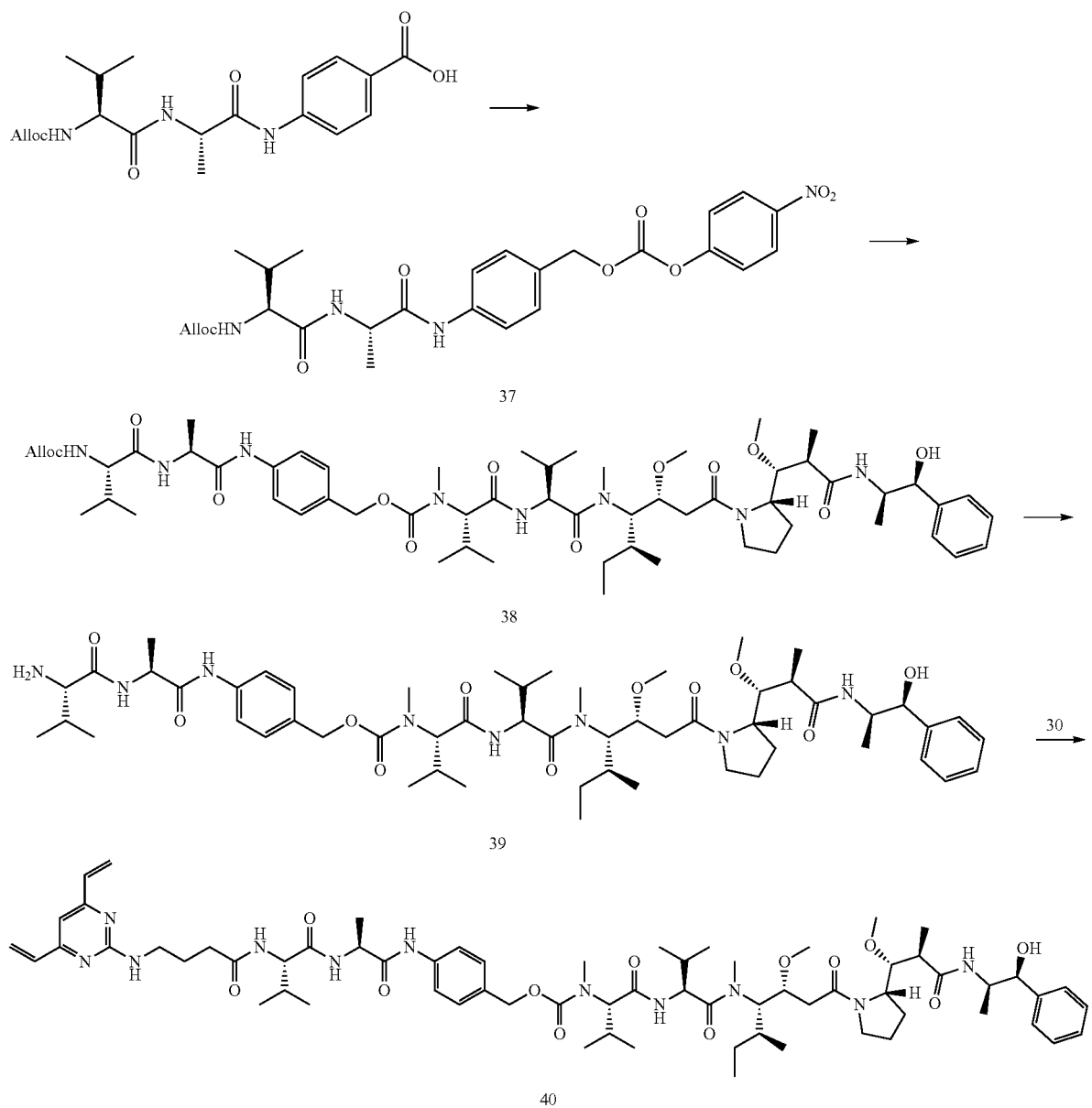

a) Alloc-Val-Ala-PAB-PNP (37)

A solution of Alloc-Val-Ala-PABA (100 mg, 0.265 mmol), bis(4-nitrophenyl) carbonate (121 mg, 0.397 mmol) and DIPEA (231 µL, 1.33 mmol) was stirred at rt for 13 h. Upon completion, the mixture was concentrated under a stream of $N_2$. The crude residue was redissolved in $CH_2Cl_2$ (20 mL) and saturated aqueous $NaHCO_3$ (25 mL), the layers separated and the aqueous phase extracted with further $CH_2Cl_2$ (3×20 mL). The combined organic fractions were dried ($MgSO_4$) and concentrated to yield Alloc-Val-Ala-PAB-PNP (125 mg, 0.230 mmol, 87%) as a pale yellow solid.

b) Alloc-Val-Ala-PABC-MMAE (38)

A solution of MMAE (40.0 mg, 74.0 µmol), Alloc-Val-Ala-PAB-PNP 37 (36 mg, 50.1 µmol), 1-hydroxybenzotriazole hydrate (16.6 mg, 123 µmol) and pyridine (50.0 µL, 614 µmol) in DMF (0.5 mL) was stirred at rt for 2 h. Upon completion, the reaction mixture was concentrated under a stream of $N_2$ and the crude residue purified by FCC (0-6% MeOH/$CH_2Cl_2$) to yield Alloc-Val-Ala-PABC-MMAE (49.5 mg, 44.1 µmol, 88%) as a white solid.

c) H-Val-Ala-PABC-MMAE (39)

A solution of Alloc-Val-Ala-PABC-MMAE 38 (37.0 mg, 33.0 µmol) and Pd(PPh$_3$)$_4$ (2.00 mg, 1.65 µmol) and pyrrolidine (5.50 µL, 66.0 µmol) in $CH_2Cl_2$ (0.6 mL) was stirred at rt for 1 h. Upon completion, the reaction mixture was diluted with $CH_2Cl_2$ (15 mL) and saturated aqueous $NaHCO_3$ (15 mL). The layers were separated and the aqueous phase was extracted with further $CH_2Cl_2$ (3×20 mL). The combined organic fractions were dried ($MgSO_4$), concentrated in vacuo and carried through without further purification.

d) DVP-Val-Ala-PABC-MMAE (40)

A solution of H-Val-Ala-PABC-MMAE 39 (12.0 mg, 11.6 µmol), 4-((4,6-divinylpyrimidin-2-yl)amino)butanoic acid 30 (6.80 mg, 29.0 µmol), HBTU (8.80 mg, 23.2 µmol), 1-hydroxybenzotriazole hydrate (3.10 mg, 23.2 µmol) and DIPEA (13.6 µL, 58.0 µmol) in DMF (1 mL) was stirred at rt for 16 h. Upon completion, the reaction was concentrated under a stream of $N_2$ and the crude residue purified by FCC (0-8% MeOH/$CH_2Cl_2$) to yield DVP-Val-Cit-PABC-MMAE (4.1 mg, 3.27 µmol, 28%) as a clear oil.

Experiment 9

Synthesis of 4-((4,6-divinylpyrimidin-2-yl)(hex-5-yn-1-yl)amino)butanoic acid (44)

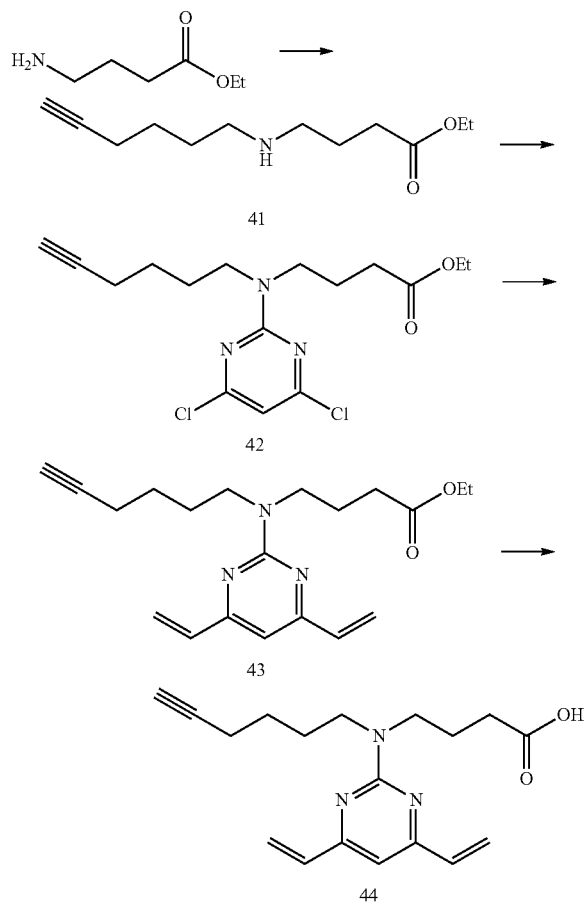

a) Ethyl 4-(hex-5-yn-1-ylamino)butanoate (41)

A solution of sulfur trioxide pyridine complex (4.87 g, 30.6 mmol) and pyridine (2.53 mL, 30.6 mmol) in CH-2C12 (10 mL) was stirred at rt for 5 min. To this solution was added DIPEA (5.33 mL, 30.6 mmol) and DMSO (7.24 mL, 102 mmol) and stirred at rt for 5 min. The mixture was cooled to −40° C. and to this was added 5-hevn-1-ol (1.00 a. 10.2 mmol). The reaction was stirred for 2 h at −40° C., followed by 1 h at −10° C. then 1 h at rt. Upon completion, the reaction was acidified to pH 3 with 1 M HCl and diluted with $CH_2Cl_2$ (10 mL). The layers were separated and the aqueous phase was extracted with further $CH_2Cl_2$ (2×20 mL). The combined organic fractions were washed with brine (2×50 mL), dried (MgSO$_4$) and concentrated in vacuo. The crude oil was immediately redissolved in MeOH (10 mL). To this solution was added ethyl 4-aminobutyrate hydrochloride (2.05 g, 12.2 mmol) and triethylamine (2.84 mL, 20.4 mmol) and the mixture stirred at room temperature for 16 h. The reaction mixture was then cooled to 0° C. and to this was added sodium borohydride (578 mg, 15.3 mmol). The reaction was warmed to rt and stirred for 2 h. Upon completion, the reaction mixture was concentrated in vacuo, redissolved in $CH_2Cl_2$ and quenched with $H_2O$. The layers were separated and the aqueous phase extracted with further $CH_2Cl_2$ (3×15 mL), dried (MgSO$_4$) and concentrated in vacuo. The crude residue was purified by FCC (0-7.5% MeOH/$CH_2Cl_2$) to yield ethyl 4-(hex-5-yn-1-ylamino)butanoate (175 mg, 0.828 mmol, 8%) as a clear oil.

b) Ethyl 4-((4,6-dichloropyrimidin-2-yl)(hex-5-yn-1-yl)amino)butanoate (42)

A solution of 2,4,6-trichloropyrimidine (68.0 µL, 0.592 mmol), ethyl 4-(hex-5-yn-1-ylamino)butanoate 41 (150 mg, 0.710 mmol) and triethylamine (165 µL, 1.18 mmol) in acetone was stirred at 0° C. for 2.5 h. Upon completion, the reaction was concentrated in vacuo and the residue redissolved in $H_2O$ (10 mL), saturated aqueous NaHCO$_3$ (10 mL) and $CH_2Cl_2$ (20 mL). The layers were separated and the aqueous phase was extracted with further $CH_2Cl_2$ (3×20 mL). The combined organic fractions were dried (MgSO$_4$), concentrated in vacuo and the crude residue purified by FCC (3-20% EtOAc/PE) to yield ethyl 4-((4,6-dichloropyrimidin-2-yl)(hex-5-yn-1-yl)amino)butanoate (32.0 mg, 89.0 µmol, 15%) as a white solid.

c) Ethyl 4-((4,6-divinylpyrimidin-2-yl)(hex-5-yn-1-yl)amino)butanoate (43)

A solution of ethyl 4-((4,6-dichloropyrimidin-2-yl)(hex-5-yn-1-yl)amino)butanoate 42 (23.0 mg, 64.2 µmol), potassium vinyltrifluoroborate (43.0 mg, 321 µmol), Pd(dppf)Cl$_2$—$CH_2Cl_2$ (8.00 mg, 9.63 µmol) and potassium carbonate (53.0 mg, 385 µmol) in THF/$H_2O$ (10:1, 1.1 mL) was heated to 70° C. for 20 h. Upon completion, the reaction mixture was filtered through Celite® and the solvent removed in vacuo. The resulting residue was purified by flash column chromatography (FCC, 5% EtOAc/PE) to yield ethyl 4-((4,6-divinylpyrimidin-2-yl)(hex-5-yn-1-yl)amino)butanoate (11.5 mg, 33.7 µmol, 53%) as a pale yellow oil.

d) 4-((4,6-divinylpyrimidin-2-yl)(hex-5-yn-1-yl)amino)butanoic acid (44)

A solution of ethyl 4-((4,6-divinylpyrimidin-2-yl)(hex-5-yn-1-yl)amino)butanoate 43 (8.00 mg, 23.4 µmol) and LiOH·$H_2O$ (4.00 mg, 93.8 µmol) in THF/$H_2O$ (0.5 mL, 1:1) was stirred at rt for 21 h. Upon completion, the reaction was diluted with $H_2O$ (10 mL) and washed with $Et_2O$ (10 mL). The aqueous phase was neutralised with 1 M HCl and extracted with $CH_2Cl_2$ (4×20 mL). The combined organic fractions were dried (MgSO$_4$) and concentrated in vacuo to yield 4-((4,6-divinylpyrimidin-2-yl)(hex-5-yn-1-yl)amino)butanoic acid (6.30 mg, 20.1 µmol, 86%) as a pale yellow oil.

| References | |
|---|---|
| Reference | DOI |
| Badescu 2014: G. Badescu, P. Bryant, M. Bird, K. Henseleit, J. Swierkosz, V. Parekh, R. Tommasi, E. Pawlisz, K. Jurlewicz, M. Farys, et al., *Bioconjug. Chem.* 2014, 25, 1124-36 | 10.1021/bc500148x |
| Beck 2017: A. Beck, L. Goetsch, C. Dumontet, N. Corvaia, *Nat. Rev. Drug Discov.* 2017, 16, 315-337 | 10.1038/nrd.2016.268 |
| Behrens 2015: C. R. Behrens, E. H. Ha, L. L. Chinn, S. Bowers, G. Probst, M. Fitch-Bruhns, J. Monteon, A. Valdiosera, A. Bermudez, S. Liao-Chan, et al., *Mol. Pharm.* 2015, 12, 3986-3998 | 10.1021/acs.molpharmaceut.5b00432 |
| Chudasma 2011: V. Chudasama, M. E. B. Smith, F. F. Schumacher, D. Papaioannou, G. Waksman, J. R. Baker, S. Caddick, *Chem. Commun.* 2011, 47, 8781 | 10.1039/c1cc12807h |
| Chudasma 2016: V. Chudasama, A. Maruani, S. Caddick, *Nat. Chem.* 2016, 8, 114-119 | 10.1038/nchem.2415 |
| Junutula 2008: J. R. Junutula, H. Raab, S. Clark, S. Bhakta, D. D. Leipold, S. Weir, Y. Chen, M. Simpson, S. P. Tsai, M. S. Dennis, et al., *Nat. Biotechnol.* 2008, 26, 925-32 | 10.1038/nbt.1480 |
| Lyon 2014: R. P. Lyon, J. R. Setter, T. D. Bovee, S. O. Doronina, J. H. Hunter, M. E. Anderson, C. L. Balasubramanian, S. M. Duniho, C. I. Leiske, F. Li, et al., *Nat. Biotechnol.* 2014, 32, 1059-62 | 10.1038/nbt.2968 |
| Maruani 2015: A. Maruani, M. E. B. Smith, E. Miranda, K. A. Chester, V. Chudasama, S. Caddick, *Nat. Commun.* 2015, 6, 6645 | 10.1038/ncomms7645 |
| Nunes 2015: J. P. M. Nunes, M. Morais, V. Vassileva, E. Robinson, V. S. Rajkumar, M. E. B. Smith, R. B. Pedley, S. Caddick, J. R. Baker, V. Chudasama, *Chem. Commun.* 2015, 51, 10624-10627 | 10.1039/c5cc03557k |
| Schumacher 2014: F. F. Schumacher, J. P. M. Nunes, A. Maruani, V. Chudasama, M. E. B. Smith, K. A. Chester, J. R. Baker, S. Caddick, *Org. Biomol. Chem.* 2014, 12, 7261-9 | 10.1039/c4ob01550a |
| Wang 2017: Y. Wang, A. G. Cheetham, G. Angacian, H. Su, L. Xie, H. Cui, *Advanced Drug Delivery Reviews* 2017, 110-111, 112 | 10.1016/j.addr.2016.06.015 |
| Zimmerman 2014: E. S. Zimmerman, T. H. Heibeck, A. Gill, X. Li, C. J. Murray, M. R. Madlansacay, C. Tran, N. T. Uter, G. Yin, P. J. Rivers, et al., *Bioconjug. Chem.* 2014, 25, 351-61 | 10.1021/bc400490z |

The invention claimed is:

1. A conjugate comprising a protein or a peptide, a linker and an active agent, wherein the linker comprises the moiety of formula (III):

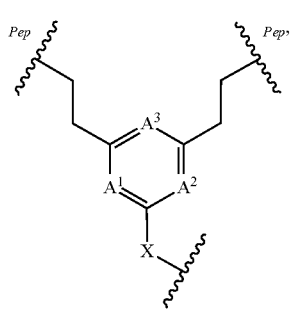

(III)

wherein two of $A^1$, $A^2$ and $A^3$ are N and the other of $A^1$, $A^2$ and $A^3$ is CH;

X is $NR^N$, where $R^N$ is H or $C_{1-2}$ alkyl, and

Pep indicates where the moiety is linked to the protein or peptide, either directly or indirectly.

2. The conjugate according to claim 1, wherein the protein is an antibody or an antigen-binding fragment thereof.

3. The conjugate according to claim 2, wherein the antibody or antigen-binding fragment thereof is directed to a tumor associated antigen.

4. The conjugate according to claim 1, wherein the active agent is a drug, which is a cytotoxin.

5. The conjugate according to claim 1, wherein $A^1$ and $A^2$ are N.

6. The conjugate according to claim 1, wherein there is a single active agent attached to X via a linker.

7. The conjugate according to claim 6, wherein the linker comprises the moiety of formula (IIIa):

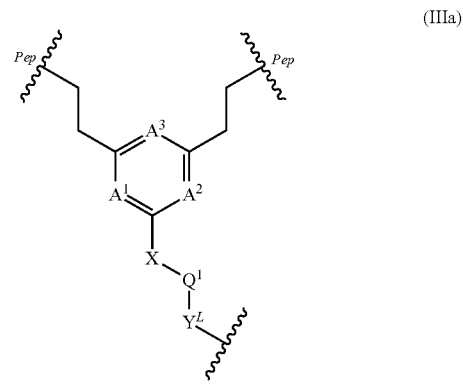

(IIIa)

wherein $Q^1$ is:

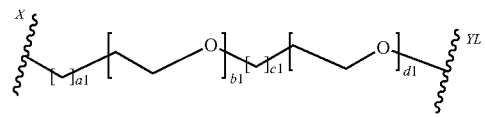

where a1=0 to 5, b1=0 to 16, c1=0 to 5, d1 is 0 to 16, and b1+d1=0 to 16;

and $Y^L$ is a functional linking moiety.

8. The conjugate according to claim 7, wherein $Y^L$ is selected from the group consisting of:

(a)

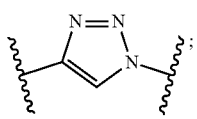 [SMILES: *c1cn(*)nn1]

and (b) —C(═O)NH—.

9. The conjugate according to claim 8, wherein the linker comprises the moiety of formula (IIIb):

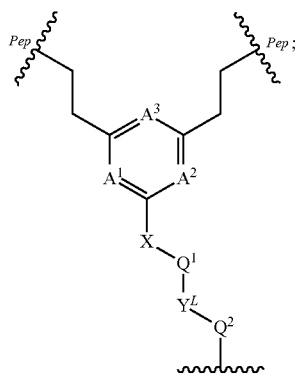
(IIIb)

where $Q^2$ is:

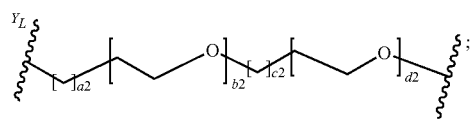

where a2=0 to 5, b2=0 to 16, c2=0 to 5, d2 is 0 to 16, and b2+d2=0 to 16.

10. The conjugate according to claim 9, wherein the linker comprises the moiety of formula (IIIc):

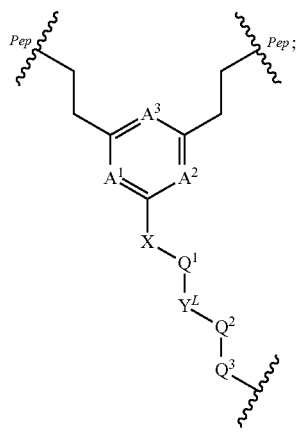
(IIIc)

where $Q^3$ is:

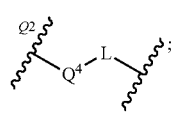

wherein $Q^4$ is a single bond, or

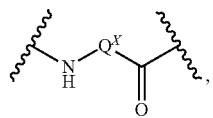

where $Q^X$ is such that $Q^4$ is an amino-acid residue, a dipeptide residue or a tripeptide residue, and L is a group for attachment to the active agent.

11. The conjugate according to claim 10, wherein L is selected from:
(a) a single bond;
(b) —C(=O)—;
(c) —NH—; and
(d)

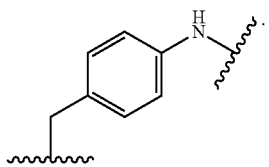 [SMILES: *Cc1ccc(N*)cc1]

12. The conjugate according to claim 11, wherein the agent-linker is of formula (IIId):

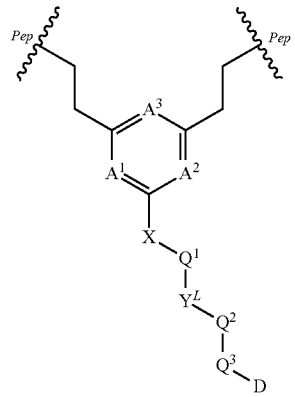
(IIId)

where D is the active agent.

13. The conjugate according to claim 1, wherein X is N and there are two active agents, each attached to X via a linker.

14. An agent-linker compound comprising a linker and an active agent, wherein the linker comprises the moiety of formula (II):

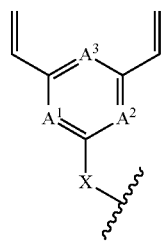
(II)

wherein $A^1$, $A^2$ and $A^3$, X and the active agent are as defined in claim 1.

15. An agent-linker compound comprising a linker and an active agent, wherein the linker comprises the moiety of formula (II):

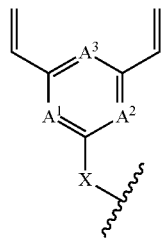

(II)

wherein $A^1$, $A^2$ and $A^3$ and the active agent are defined in claim 1, wherein X is $NR^N$, where $R^N$ is H or $C_{1-2}$ alkyl, and there are two active agents, each attached to X via a linker.

16. A compound of formula (Ia):

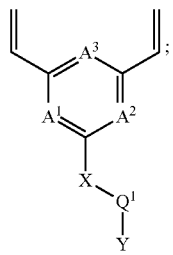

(Ia)

wherein:
$A^1$, $A^2$, $A^3$, and X are as defined in claim 1;
$Q^1$ is

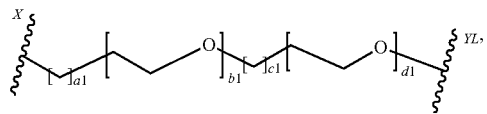

where a1=0 to 5, b1=0 to 16, c1=0 to 5, d1 is 0 to 16, and b1+d=0 to 16, and $Y^L$ is a functional linking moiety; and
Y is a group capable reacting with another moiety to form $Y^L$.

17. A compound according to claim 16, wherein Y is selected from the group consisting of:
(a) —C≡CH;
(b) —C(=O)OH;
(c) —$N_3$; and
(d) —$NH_2$.

18. A compound of formula (Ic):

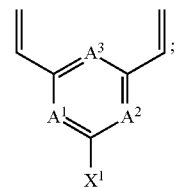

(Ic)

wherein:
$A^1$, $A^2$ and $A^3$ are as defined in claim 1;
$X^1$ is $NH_2$.

19. A pharmaceutical composition comprising, a conjugate according to claim 1, and a carrier, excipient or diluent.

20. A method of treating a proliferative disease comprising administering a therapeutically effective amount of a conjugate according to claim 4 to a patient in need thereof.

* * * * *